US011629183B2

(12) United States Patent
Giasson et al.

(10) Patent No.: US 11,629,183 B2
(45) Date of Patent: Apr. 18, 2023

(54) MONOCLONAL ANTIBODIES TARGETING MICROTUBULE-BINDING DOMAIN OF TAU PROTEIN AND METHODS OF DETECTING TAU PROTEIN IN VIVO

(71) Applicant: University of Florida Research Foundation, Inc., Gainesville, FL (US)

(72) Inventors: Benoit Giasson, Gainesville, FL (US); Todd Eliot Golde, Gainesville, FL (US); Cara Louise Croft, Gainesville, FL (US); Yona Levites, Gainesville, FL (US); Brenda Dawn Moore, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 312 days.

(21) Appl. No.: 16/958,823

(22) PCT Filed: Dec. 28, 2018

(86) PCT No.: PCT/US2018/067840
§ 371 (c)(1),
(2) Date: Jun. 29, 2020

(87) PCT Pub. No.: WO2019/133799
PCT Pub. Date: Jul. 4, 2019

(65) Prior Publication Data
US 2021/0070847 A1  Mar. 11, 2021

Related U.S. Application Data

(60) Provisional application No. 62/647,899, filed on Mar. 26, 2018, provisional application No. 62/611,556, filed on Dec. 29, 2017.

(51) Int. Cl.
| | | |
|---|---|---|
| *A61K 39/395* | (2006.01) | |
| *A61K 39/00* | (2006.01) | |
| *C07K 16/18* | (2006.01) | |
| *C07K 16/00* | (2006.01) | |
| *G01N 33/53* | (2006.01) | |
| *G01N 33/68* | (2006.01) | |
| *A61B 5/00* | (2006.01) | |
| *G01N 33/533* | (2006.01) | |
| *G01N 33/535* | (2006.01) | |

(52) U.S. Cl.
CPC ............ *C07K 16/18* (2013.01); *A61B 5/0073* (2013.01); *G01N 33/533* (2013.01); *G01N 33/535* (2013.01); *C07K 2317/565* (2013.01)

(58) Field of Classification Search
CPC ............... C07K 16/18; C07K 14/4711; C07K 2317/54; C07K 2317/55; C07K 2317/622; C07K 2317/565; C07K 2317/56; C07K 2317/34; C07K 2317/76; C07K 2317/515; C07K 317/70; A61K 39/0007; A61K 2039/505; A61K 39/395; A61P 25/28; A61P 25/00; G01N 33/6896; G01N 2800/2821; G01N 2800/52; G01N 2800/28; G01N 2333/4709; G01N 2440/14; G01N 33/53; G01N 3/5058; G01N 2800/7047; G01N 2800/50

See application file for complete search history.

(56) References Cited

U.S. PATENT DOCUMENTS

| | | | |
|---|---|---|---|
| 2012/0321557 A1 | 12/2012 | Kimura | |
| 2015/0344553 A1 | 12/2015 | Weinreb et al. | |
| 2017/0210787 A1 | 7/2017 | Wadia et al. | |

FOREIGN PATENT DOCUMENTS

| | | |
|---|---|---|
| WO | 2012163805 A1 | 12/2012 |
| WO | 2015032932 A1 | 3/2015 |
| WO | 2015095766 A2 | 6/2015 |
| WO | 2017205377 A2 | 11/2017 |

OTHER PUBLICATIONS

MacCallum et al., J. Mol. Biol.,1996; 262:732-745.*
Pascalis et al.,The Journal of Immunology, 2002; 169: 3076-3084.*
Casset et al., BBRC, 2003; 307: 198-205.*
Vajdos et al., J. Mol. Biol. 2002; 320: 415-428.*
Holm et al., Mol. Immunol., 2007; 44: 1075-1084.*
Chen et al.,J. Mol. Bio., 1999; 293: 865-881.*
Wu et al., J. Mol. Biol., 1999; 294:151-162.*
Burgess et al. J of Cell Bio. 1990, 111:2129-2138.*
Bowie et al. Science, 1990, 247:1306-1310.*
Alaoui-Ismaili et al., Cytokine Growth Factor Rev. 2009; 20:501-507.*
Guo et al., PNAS 2004; 101:9205-9210.*
Rudikoff et al.,Proc. Natl. Acad. Sci. USA 1982 vol. 79: p. 1979.*
Pawson et al. 2003, Science 300:445-452.*
International Search Report issued for PCT/US2018/067840, dated Mar. 8, 2019.
Croft et al., Novel Monoclonal Antibodies Targeting the Microtubule-Binding Domain of Human Tau, PLoS One, vol. 13, Iss. 4, pp. 1-13, 2018.
Strang et al., Generation and Characterization of New Monoclonal Antibodies Targeting the PHF1 and AT8 Epitopes on Human Tau, Acta Neuropathologica Communications, vol. 5, No. 1, pp. 1-11, 2017.

* cited by examiner

*Primary Examiner* — Chang-Yu Wang
(74) *Attorney, Agent, or Firm* — Thomas | Horstemeyer, LLP

(57) ABSTRACT

Disclosed herein are monoclonal antibodies targeting specific tau epitopes, particularly, microtubule binding domain region 2 or region 4. Also disclosed herein are antibodies or antigen binding fragments thereof that specifically recognize a tau epitope consisting of the amino acid sequence of SEQ ID NO: 9 or 11. Also disclosed herein are methods of detecting tau protein in a subject, comprising performing an assay using the antibodies or antigen binding fragments thereof on the subject or on a biological sample obtained from the subject. Assay kits containing the disclosed antibodies are also provided. Further, methods of treating or preventing a tauopathy in a subject by administering to the subject tau antibodies or antigen-binding fragments thereof are provided.

10 Claims, 14 Drawing Sheets
Specification includes a Sequence Listing.

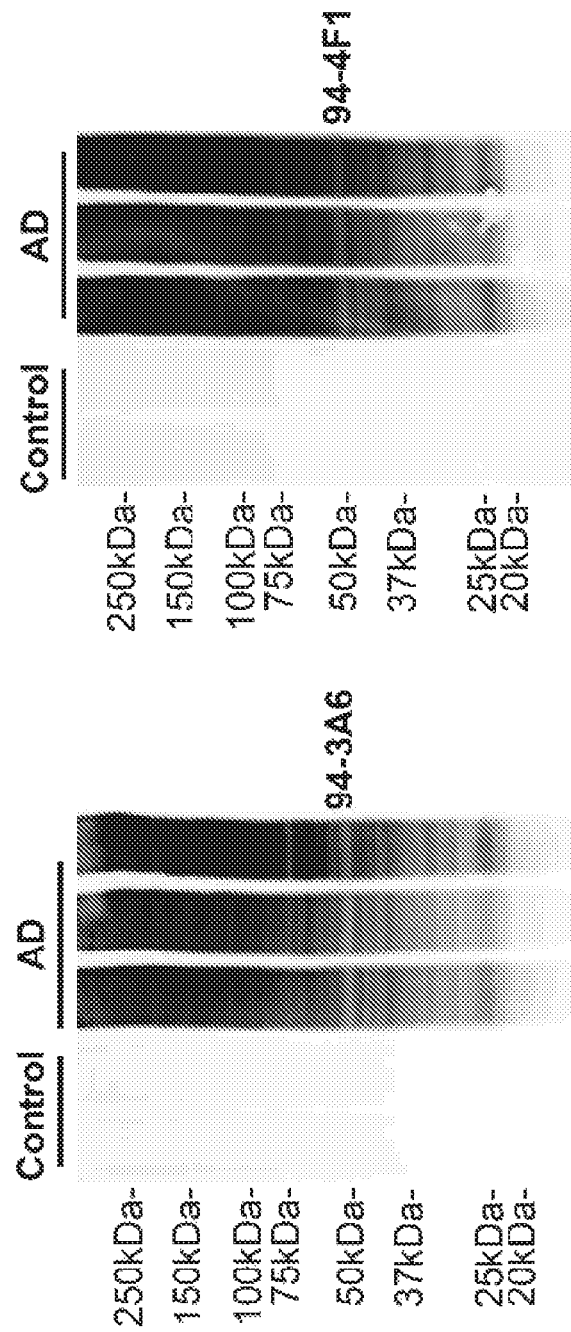

MONOCLONAL ANTIBODIES TARGETING MICROTUBULE-BINDING DOMAIN OF TAU PROTEIN AND METHODS OF DETECTING TAU PROTEIN IN VIVO

CROSS-REFERENCE TO RELATED APPLICATIONS

This application is a National Stage of International Application No. PCT/US2018/067840, filed Dec. 28, 2018, which claims benefit of U.S. Provisional Application Ser. No. 62/611,556, filed Dec. 29, 2017, and Application No. 62/647,899, filed Mar. 26, 2018, which are hereby incorporated herein by reference in its entirety.

STATEMENT REGARDING FEDERALLY SPONSORED RESEARCH OR DEVELOPMENT

This invention was made with government support under Grant Nos. NS089622 and AG047266 awarded by the National Institutes of Health. The government has certain rights in the invention.

SEQUENCE LISTING

This application contains a sequence listing filed in electronic form as an ASCII.txt file entitled "222110-2630 Sequence Listing_ST25" created on Dec. 23, 2018. The content of the sequence listing is incorporated herein in its entirety.

BACKGROUND

Tauopathies are a group of neurodegenerative diseases predominantly identifiable by inclusions composed of aggregated, highly phosphorylated and cleaved microtubule (MT)-associated protein tau (MAPT). This burden of tau inclusion pathology has been shown to correlate with the cognitive decline observed in these diseases, as well as, neurodegeneration. Indeed, cognitive decline associates more with the tau burden compared to the amyloid-β load in Alzheimer's disease (AD). Tauopathies are pathologically and symptomatically heterogeneous and include AD, Progressive Supranuclear Palsy (PSP), corticobasal degeneration (CBD), Pick's disease and frontotemporal dementia with parkinsonism linked to chromosome 17 (FTDP-17).

Tau exists in six isoforms, ranging from 352 to 441 amino acids as a result of alternative splicing of exons 2, 3 and 10 (Goedert M, et al. Neuron. 1989 3(4):519-26; Himmler A. Mol Cell Biol 1989 9(4):1389-96; Goedert M, et al. EMBO J. 1989 8(2):393-9) and is natively unfolded. Specifically, alternative splicing of exon 10 leads to the exclusion or inclusion of the second MT binding repeat (R2), producing tau isoforms with either 3 (3R: $1^{st}$, $3^{rd}$ and $4^{th}$ repeats) or 4 ($1^{st}$ $2^{nd}$, $3^{rd}$ and $4^{th}$ repeats) MT repeats, respectively. Inclusion of exons 2 and 3 results in tau isoforms with N-terminal inserts termed N1 and N2, respectively. Tau expression is developmentally regulated; human fetal brain expresses only the shortest tau isoform (0N3R) whereas in healthy adult brain equal amounts of 3R and 4R tau are expressed. Differences between 3R and 4R tau amounts can exist in certain diseases. Some FTDP-17 mutations increase the ratio of 4R to 3R tau and insoluble tau purified from these cases are largely 4R tau, similar to findings observed in PSP and CBD. PiD, on the other hand shows increased amounts of 3R to 4R tau and in AD, equivalent amounts of both isoforms are found.

The MT binding domain (MTBD) of tau enables it to bind, assemble and stabilize MTs, promoting neuronal stability. The number of MT repeats (3R or 4R) in tau can affect the speed of axonal transport and the presence of 4 MTBDs increases the propensity of tau to form β-sheets and aggregate. The MTBD is the core domain required to drive amyloid structure formation and aggregation. Phosphorylation in the MTBD decreases the affinity of tau for MTs and may contribute to the accumulation of unbound tau in pathological inclusions.

Identifying 3R and 4R tau is relevant as pathological markers to distinguish between tauopathies. Also, targeting the MT-binding repeat domain of tau using an antibody can provide immunotherapy for tauopathies. Disclosed herein are monoclonal antibodies targeting this region of tau enabling the study of these different isoforms and to therapeutically target tau pathology.

SUMMARY

Monoclonal antibodies that specifically recognize certain tau epitopes, particularly, MTBD repeat domains, are provided. Therefore, disclosed herein are antibodies or antigen binding fragments thereof that specifically recognize epitopes of tau in MTBD repeat domains. In particular embodiments, the antibodies or antigen binding fragments thereof recognize epitopes of tau consisting of the amino acid sequence of SEQ ID NO: 9 (MTBD R2 (residues 275-305 of 2N/4R tau (SEQ ID NO: 1)) or specifically bind to peptides containing the amino acid sequence of SEQ ID NO: 11 (MTBD R4 (residues 337-372 relative to 2N/4R tau)).

The disclosed antibodies or antigen binding fragments thereof can be monoclonal antibodies, such as murine monoclonal antibodies, human monoclonal antibodies, chimeric antibodies, human antibodies, humanized antibodies, intrabodies, single chain antibodies, single chain fragment variable (scFv) antibodies, or fragment antigen-binding (Fab fragment).

Also disclosed herein are methods of detecting tau protein in an animal, the method comprising performing an assay using the antibodies or antigen binding fragments thereof described herein on a subject or on a biological sample obtained from a subject. The assay can be an ELISA, for example, sandwich ELISA or competitive ELISA.

Also provided are kits, for example ELISA kits, comprising the disclosed antibody or antigen binding fragment thereof. The antibodies or antigen binding fragments thereof can be labeled with an enzyme in the disclosed ELISA kits. Alternately, the antibodies or antigen binding fragments thereof can be coated on to immunoassay plates.

Also disclosed are methods of treating or preventing tauopathies in a subject by administering to the subject one or more tau antibodies or antigen-binding fragments thereof as disclosed herein.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 5A to 5E. Characterization of the disclosed tau antibodies in sarkosyl-insoluble human control and AD cortex. Immunoblots of biochemically sarkosyl-insoluble temporal cortex lysates from post-mortem control (n=2) and AD (n=3) cases were probed with the disclosed tau antibodies (as indicated for each blot) 81A11, 83E4, 94-3A2-2, 94-3A6 and 94-4F1 to determine affinity for tau in human AD. The mobilities of molecular mass markers are shown on the left.

BRIEF DESCRIPTION OF THE SEQUENCES

Figures 1A, 1B, 1C:
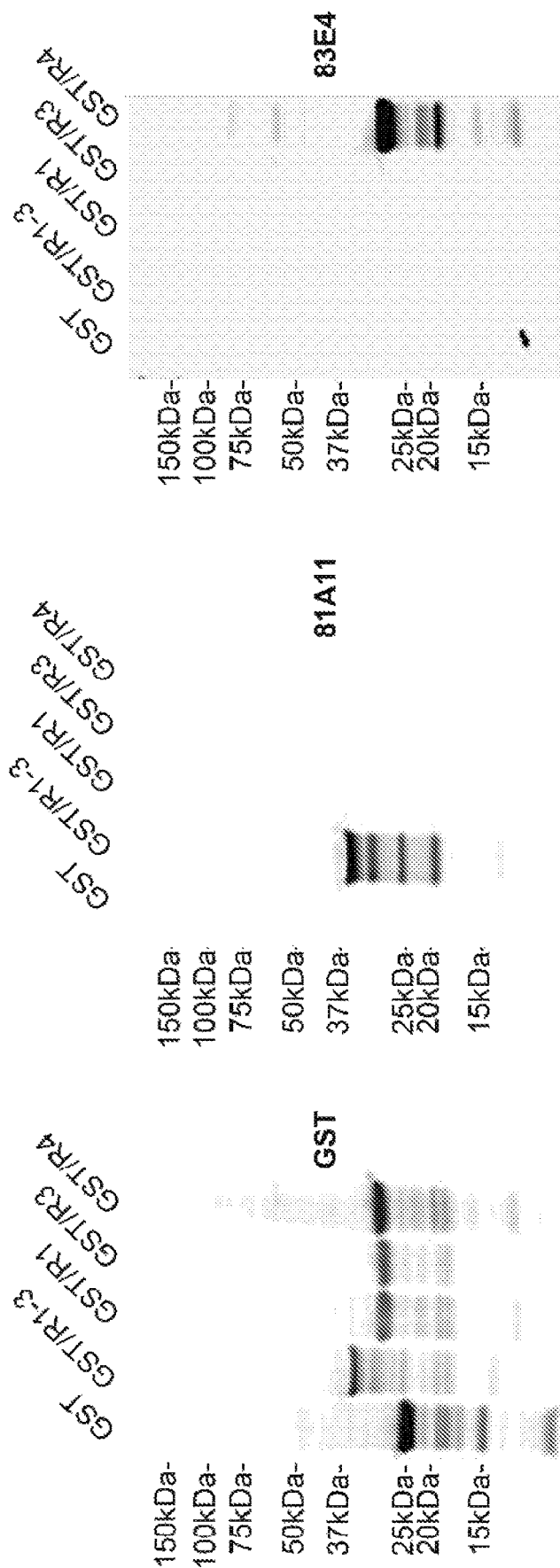
FIGS. 1A to 1F show specificity of the disclosed tau antibodies to the MT-binding repeat domains of tau. Immunoblots of recombinant glutathione-S-transferase (GST), GST/R1-3, GST/R1, GST/R3 and GST/R4 human tau probed with anti-GST antibody (FIG. 1A) and the disclosed tau antibodies 81A11 (FIG. 1B), 83E4 (FIG. 1C), 94-3A2-2 (FIG. 1F), 94-3A6 (FIG. 1D), 94-4F1 (FIG. 1E) to determine epitopes. The mobilities of molecular mass markers are shown on the left.

SEQ ID NO: 1: Sequence of 2N/4R human tau.
MAEPRQEFEVMEDHAGTYGLGDRKDQGGYTMHQDQEGDTDAGLKESPLQT
PTEDGSEEPGSETSDAKSTPTAEDVTAPLVDEGAPGKQAAAQPHTEIPEG
TTAEEAGIGDTPSLEDEAAGHVTQARMVSKSKDGTGSDDKKAKGADGKTK
IATPRGAAPPGQKGQANATRIPAKTPPAPKTPPSSGEPPKSGDRSGYSSP
GSPGTPGSRSRTPSLPTPPTREPKKVAVVRTPPKSPSSAKSRLQTAPVPM
PDLKNVKSKIGSTENLKHQPGGGKVQIINKKLDLSNVQSKCGSKDNIKHV
PGGGSVQIVYKPVDLSKVTSKCGSLGNIHHKPGGGQVEVKSEKLDFKDRV
QSKIGSLDNITHVPGGGNKKIETHKLTFRENAKAKTDHGAEIVYKSPVVS
GDTSPRHLSNVSSTGSIDMVDSPQLATLADEVSASLAKQGL SEQ ID NO: 2: Sequence of 1N/4R human tau.
MAEPRQEFEVMEDHAGTYGLGDRKDQGGYTMHQDQEGDTDAGLKESPLQT
PTEDGSEEPGSETSDAKSTPTAEAEEEAGIGDTPSLEDEAAGHVTQARMVS
KSKDGTGSDDKKAKGADGKTKIATPRGAAPPGQKGQANATRIPAKTPPAP
KTPPSSGEPPKSGDRSGYSSPGSPGTPGSRSRTPSLPTPPTREPKKVAVV
RTPPKSPSSAKSRLQTAPVPMPDLKNVKSKIGSTENLKHQPGGGKVQIIN
KKLDLSNVQSKCGSKDNIKHVPGGGSVQIVYKPVDLSKVTSKCGSLGNIH
HKPGGGQVEVKSEKLDFKDRVQSKIGSLDNITHVPGGGNKKIETHKLTFR
ENAKAKTDHGAEIVYKSPVVSGDTSPRHLSNVSSTGSIDMVDSPQLATLA
DEVSASLAKQGL SEQ ID NO: 3: Sequence of 0N/4R human tau.
MAEPRQEFEVMEDHAGTYGLGDRKDQGGYTMHQDQEGDTDAGLKAEEAGI
GDTPSLEDEAAGHVTQARMVSKSKDGTGSDDKKAKGADGKTKIATPRGAA
PPGQKGQANATRIPAKTPPAPKTPPSSGEPPKSGDRSGYSSPGSPGTPGS
RSRTPSLPTPPTREPKKVAVVRTPPKSPSSAKSRLQTAPVPMPDLKNVKS
KIGSTENLKHQPGGGKVQIINKKLDLSNVQSKCGSKDNIKHVPGGGSVQI
VYKPVDLSKVTSKCGSLGNIHHKPGGGQVEVKSEKLDFKDRVQSKIGSLD
NITHVPGGGNKKIETHKLTFRENAKAKTDHGAEIVYKSPVVSGDTSPRHL
SNVSSTGSIDMVDSPQLATLADEVSASLAKQGL SEQ ID NO: 4: Sequence of 2N/3R human tau
MAEPRQEFEVMEDHAGTYGLGDRKDQGGYTMHQDQEGDTDAGLKESPLQT
PTEDGSEEPGSETSDAKSTPTAEDVTAPLVDEGAPGKQAAAQPHTEIPEG
TTAEEAGIGDTPSLEDEAAGHVTQARMVSKSKDGTGSDDKKAKGADGKTK
IATPRGAAPPGQKGQANATRIPAKTPPAPKTPPSSGEPPKSGDRSGYSSP
GSPGTPGSRSRTPSLPTPPTREPKKVAVVRTPPKSPSSAKSRLQTAPVPM
PDLKNVKSKIGSTENLKHQPGGGKVQIVYKPVDLSKVTSKCGSLGNIHHK
PGGGQVEVKSEKLDFKDRVQSKIGSLDNITHVPGGGNKKIETHKLTFREN
AKAKTDHGAEIVYKSPVVSGDTSPRHLSNVSSTGSIDMVDSPQLATLADE
VSASLAKQGL SEQ ID NO: 5: Sequence of 1N/3R human tau
MAEPRQEFEVMEDHAGTYGLGDRKDQGGYTMHQDQEGDTDAGLKESPLQT
PTEDGSEEPGSETSDAKSTPTAEAEEAGIGDTPSLEDEAAGHVTQARMVS
KSKDGTGSDDKKAKGADGKTKIATPRGAAPPGQKGQANATRIPAKTPPAP
KTPPSSGEPPKSGDRSGYSSPGSPGTPGSRSRTPSLPTPPTREPKKVAVV
RTPPKSPSSAKSRLQTAPVPMPDLKNVKSKIGSTENLKHQPGGGKVQIVY
KPVDLSKVTSKCGSLGNIHHKPGGGQVEVKSEKLDFKDRVQSKIGSLDNI
THVPGGGNKKIETHKLTFRENAKAKTDHGAEIVYKSPVVSGDTSPRHLSN
VSSTGSIDMVDSPQLATLADEVSASLAKQGL SEQ ID NO: 6: Sequence of 0N/3R human tau
MAEPRQEFEVMEDHAGTYGLGDRKDQGGYTMHQDQEGDTDAGLKAEEAGI

GDTPSLEDEAAGHVTQARMVSKSKDGTGSDDKKAKGADGKTKIATPRGAA

PPGQKGQANATRIPAKTPPAPKTPPSSGEPPKSGDRSGYSSPGSPGTPGS

RSRTPSLPTPPTREPKKVAVVRTPPKSPSSAKSRLQTAPVPMPDLKNVKS

KIGSTENLKHQPGGGKVQIVYKPVDLSKVTSKCGSLGNIHHKPGGGQVEV

KSEKLDFKDRVQSKIGSLDNITHVPGGGNKKIETHKLTFRENAKAKTDHG

AEIVYKSPVVSGDTSPRHLSNVSSTGSIDMVDSPQLATLADEVSASLAKQ

GL

SEQ ID NO: 7: MTBD R1-3 (residues 244-336 of
2N/4R tau)
QTAPVPMPDLKNVKSKIGSTENLKHQPGGGKVQIINKKLDLSNVQSKCGS

KDNIKHVPGGGSVQIVYKPVDLSKVTSKCGSLGNIHHKPGGGQ

SEQ ID NO: 8: MTBD R1 (residues 244-274 of 2N/4R
tau)
QTAPVPMPDLKNVKSKIGSTENLKHQPGGGK SEQ ID NO: 9: MTBD R2 (residues 275-305 of 2N/4R
tau)
VQIINKKLDLSNVQSKCGSKDNIKHVPGGGS SEQ ID NO: 10: MTBD R3 (residues 306-336 of 2N/4R
tau)
VQIVYKPVDLSKVTSKCGSLGNIHHKPGGGQ SEQ ID NO: 11: MTBD R4 (residues 337-372 of 2N/4R
tau)
VEVKSEKLDFKDRVQSKIGSLDNITHVPGGGNKKIE SEQ ID NO: 12: MTBD R1-R4 or K18 (residues 244-372
of 2N/4R tau)
QTAPVPMPDLKNVKSKIGSTENLKHQPGGGKVQIINKKLDLSNVQSKCGS

KDNIKHVPGGGSVQIVYKPVDLSKVTSKCGSLGNIHHKPGGGQVEVKSEK

LDFKDRVQSKIGSLDNITHVPGGGNKKIE

SEQ ID NO: 13: Light chain sequence of antibody
81A11
DIVLTQSPASLAVSLGQRATISYRASKSVSTSGYSYMHWNQQKPGQPPRL

LIYLVSNLESGVPARFSGSGSGTDFTLNIHPVEEEDAATYYCQHIRELTR

SEGGPSWKLEIKRADAAPTVSIFPPSSEQLTSGGASVV

SEQ ID NO: 14: Heavy chain sequence of antibody
81A11
QVQLQQSGAELVRPGASVTLSCKASGYTFTDYEIHWVKQTPVYGLEWIGA

IDPETDTIDFNQKFKGKAILTADKSSSTAYMELRSLTSEDSAVYYSLHWD

YWGQGTTLTVSSA

SEQ ID NO: 15: CDR1 sequence of light chain of
antibody 81A11
KSVSTSGYSY

SEQ ID NO: 16: CDR2 sequence of light chain of
antibody 81A11
LVSN

SEQ ID NO: 17: CDR3 sequence of light chain of
antibody 81A11
QHIRELTRSEGGPS

SEQ ID NO: 18: CDR1 sequence of heavy chain of
antibody 81A11
GYTFTDYE

SEQ ID NO: 19: CDR2 sequence of heavy chain of
antibody 81A11
IDPETDTI

SEQ ID NO: 20: CDR3 sequence of heavy chain of
antibody 81A11
SLHWD

SEQ ID NO: 21: Light chain sequence of antibody
94-3A6
ENVLTQSPAIMSASPGEKVTMTCSASSNVNYMHWFQQESSTSPKLWIYDT

SKLASGVPGRFSGSGSGNSYSLTISSMEAEDVATYYCFQGSGYPYTFGGG

TKLEIKRADAAPTVSIFPPSSEQLTSGGASVV

SEQ ID NO: 22: Heavy chain sequence of antibody
94-3A6
QVQLQQPGTELVKPGASVKLSCKASGYPFTNYWMHWVKQRPGQGLEWIGN

INPTNGDTNYNEKFKSKATLTVDKSSSTAYMQLSSLTSEDSAVYYCTRVT

YWGQGTTLTVSSA

SEQ ID NO: 23: CDR1 sequence of light chain of
antibody 94-3A6
SNVNY

SEQ ID NO: 24: CDR2 sequence of light chain of
antibody 94-3A6
DTSK

SEQ ID NO: 25: CDR3 sequence of light chain of
antibody 94-3A6
FQGSGYP

SEQ ID NO: 26: CDR1 sequence of heavy chain of
antibody 94-3A6
GYPFTNYW

SEQ ID NO: 27: CDR2 sequence of heavy chain of
antibody 94-3A6
INPTNGDT

SEQ ID NO: 28: CDR3 sequence of heavy chain of
antibody 94-3A6
CTRVT

SEQ ID NO: 29: Light chain sequence of antibody
94-3A2.
DIVLTQSPASLAVSLGQRATISYRASKSVSTSGYSYMHWNQQKPGQPPRL

LIYLVSNLESGVPARFSGSGSGTDFTLNIHPVEEEDAATYYCQHIRELTR

SEGGPSWKKLEIKRADAAPTVSIFPPSSEQLTSGGASVV

SEQ ID NO: 30: Heavy chain sequence of antibody
94-3A2
QVQLQQSGAELAKPGASVKMSCKASGYTFTTYWMHWIKQRPGQGLEWIGY

INPSNDYTEYNQKFKDEATLTVDKSSSTAYMQLNSLISEDSAVYYCAHPA

YWGQGTLVTVSPA

SEQ ID NO: 31: CDR1 sequence of light chain of
antibody 94-3A2
KSVSTSGYSY

SEQ ID NO: 32: CDR2 sequence of light chain of
antibody 94-3A2
LVSN

SEQ ID NO: 33: CDR3 sequence of light chain of
antibody 94-3A2
QHIRELTRSEGGPS

SEQ ID NO: 34: CDR1 sequence of heavy chain of
antibody 94-3A2
GYTFTTYW

-continued

SEQ ID NO: 35: CDR2 sequence of heavy chain of
antibody 94-3A2
INPSNDYT

SEQ ID NO: 36: CDR3 sequence of heavy chain of
antibody 94-3A2
CAHPA

SEQ ID NO: 37: A tetrapeptide which prevents the
intrabody from being secreted from the ER
KDEL SEQ ID NO: 38: Light chain sequence of antibody
94-3A2-2
ENVLTQSPAIMSASPGEKVTMTCSASSSVNYMHWYQQKSGTSPKLWIYDT

SKLASGVPGRFSGSGSGNSYSLTISSMEAEDVATYYCFQGSGYPFTFGSG

TKLEIKRADAAPTVSIFPPSSEQLTSGGASVV

SEQ ID NO: 39: Heavy chain sequence of antibody
94-3A2-2
QVQLQQSGAELAKPGASVKMSCKASGYTFTTYWMHWIKQRPGQGLEWIGY

INPSNDYTEYNQKFKDEATLTVDKSSSTAYMQLNSLISEDSAVYYCAHPA

YWGQGTLVTVSSA

SEQ ID NO: 40: CDR1 sequence of light chain of
antibody 94-3A2-2
SSVNY

SEQ ID NO: 41: CDR2 sequence of light chain of
antibody 94-3A2-2
DTSK

SEQ ID NO: 42: CDR3 sequence of light chain of
antibody 94-3A2-2
FQGSGYP

SEQ ID NO: 43: CDR1 sequence of heavy chain of
antibody 94-3A2-2
GYTFTTYW

SEQ ID NO: 44: CDR2 sequence of heavy chain of
antibody 94-3A2-2
INPSNDYT

SEQ ID NO: 45: CDR3 sequence of heavy chain of
antibody 94-3A2-2
CAHPA

DETAILED DESCRIPTION

As used herein, the singular forms "a", "an" and "the" are intended to include the plural forms as well, unless the context clearly indicates otherwise. Further, to the extent that the terms "including", "includes", "having", "has", "with" or variants thereof are used in either the detailed description and/or the claims, such terms are intended to be inclusive in a manner similar to the term "comprising".

As used herein, the term "preventing" includes providing prophylaxis with respect to occurrence or recurrence of a particular disease, disorder, or condition in a subject. A subject may be predisposed to, susceptible to a particular disease, disorder, or condition, or at risk of developing such a disease, disorder, or condition, but has not yet been diagnosed with the disease, disorder, or condition.

As used herein, the term "treating" refers to clinical intervention designed to alter the natural course of a clinical pathology in a subject being treated. Desirable effects of treating a subject include decreasing the rate of progression, ameliorating or palliating the pathological state and remission or improved prognosis of a particular disease, disorder, or condition. A subject is successfully "treated", for example, if one or more symptoms associated with a particular disease, disorder, or condition are mitigated or eliminated.

An "effective amount" refers to at least an amount effective, at dosages and for periods of time necessary, to achieve the desired therapeutic or prophylactic result. An effective amount can be provided in one or more administrations.

A "therapeutically effective amount" is at least the minimum concentration required to effect a measurable improvement of a particular disease, disorder, or condition. A therapeutically effective amount herein may vary according to factors such as the disease state, age, sex, weight of the patient and the ability of the tau antibody to elicit a desired response in the subject.

A "subject" for purposes of treating or preventing refers to any animal, such as a mammal, including humans, domestic and farm animals, such as dogs, horses, rabbits, cattle, pigs, hamsters, gerbils, mice, ferrets, rats, or cats. In some embodiments, the subject is a human.

The term "antibody" is used here in a broad sense and covers a protein that includes an epitope recognition site. The term "antibody" includes polyclonal antibodies, monoclonal antibodies, murine monoclonal antibodies, human monoclonal antibodies, humanized antibodies, chimeric antibodies, human antibodies, antibody fragments (e.g., Fab, Fab'-SH, Fv, scFv and F(ab')$_2$ fragments), antibodies having modified effector functions, fusion proteins containing an antibody portion, intrabodies, glycosylation variants of antibodies, amino acid sequence variants of antibodies, covalently modified antibodies and any other modified configuration that includes an epitope recognition site.

The basic 4-chain antibody unit is a heterotetrameric glycoprotein composed of two identical light (L) chains and two identical heavy (H) chains. The pairing of a VH and VL together forms a single antigen-binding site. The structure and properties of the different classes of antibodies are described in the art, for example, in Basic and Clinical Immunology, 8th Ed., Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa ("κ") and lambda ("λ"), based on the amino acid sequences of their constant domains. Depending on the amino acid sequence of the constant domain of their heavy chains (CH), antibodies belong to one of the five classes: IgA, IgD, IgE, IgG and IgM, having heavy chains designated alpha ("α"), delta ("δ"), epsilon ("ε"), gamma ("γ") and mu ("μ"), respectively. The γ and α classes are further divided into subclasses (isotypes) on the basis of relatively minor differences in the CH sequence and function. These subclasses in humans include: IgG1, IgG2, IgG3, IgG4, IgA1 and IgA2. The subunit structures and three dimensional configurations of different classes of antibodies are known in the art and are described in, for example, Abbas et al., Cellular and Molecular Immunology, 4$^{th}$ ed. (W.B. Saunders Co., 2000).

The "variable region" or "variable domain" of an antibody refers to the amino-terminal domains of the heavy or light chain of the antibody. The variable domains of the heavy chain and light chain may be referred to as "VH" and "VL", respectively. These domains are generally the most variable parts of the antibody (relative to other antibodies of the same class) and contain the antigen binding sites.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains and is concentrated in three segments called complementarity determining region (CDR). CDRs are present in both in the light-chain and the heavy chain variable domains. The more highly conserved portions of variable domains are called the framework regions. The CDRs in each chain are held together in close proximity by the framework regions and, with the CDRs from the other chain, contribute to the formation of the antigen binding site of antibodies (see Kabat et al., Sequences of Immunological Interest, Fifth Edition, National Institute of Health, Bethesda, Md. (1991)). The constant domains are not directly involved in the binding of antibody to an antigen, but exhibit various effector functions, such as participation of the antibody in antibody-dependent-cellular toxicity.

The terms "full-length antibody", refer to an antibody in its substantially intact form, as opposed to an antibody fragment. Specifically full-length antibodies include those with heavy and light chains including an Fc region.

An "antibody fragment" comprises a portion of a full-length antibody, the antigen binding and/or the variable region of the intact antibody. Examples of antibody fragments include Fab, Fab', F(ab')$_2$ and Fv fragments; diabodies; linear antibodies (see U.S. Pat. No. 5,641,870; Zapata et al., Protein Eng. 8(10):1057-1062 (1995)); single-chain antibody molecules and multispecific antibodies formed from antibody fragments.

Papain digestion of antibodies produces two identical antigen-binding fragments, called "Fab" fragments and a residual "Fc" fragment, a designation reflecting the ability to crystallize readily. The Fab fragment consists of an entire L chain along with the variable region domain of the H chain (VH) and the first constant domain of one heavy chain (CH1). Each Fab fragment has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfide bonds. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in a non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "scFv" are antibody fragments that comprise the VH and VL antibody domains connected into a single polypeptide chain. In some embodiments, the scFv polypeptide further comprises a polypeptide linker between the VH and VL domains which enables the scFv to form the desired structure for antigen binding. For a review of the scFv, see Pluckthun in The Pharmacology of Monoclonal Antibodies, vol. 113, Rosenburg and Moore eds., Springer-Verlag, New York, pp. 269-315 (1994).

As used herein, a "chimeric antibody" refers to an antibody in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Nat'l Acad. Sci. USA, 81:6851-55 (1984)). As used herein, "humanized antibody" is used a subset of "chimeric antibodies".

"Humanized" forms of non-human (e.g., murine) antibodies are chimeric antibodies that contain minimal sequence derived from non-human immunoglobulin. In one embodiment, a humanized antibody is a human antibody (recipient antibody) in which residues from an CDR of the recipient are replaced by residues from an CDR of a non-human species (donor antibody) such as mouse, rat, rabbit or non-human primate having the desired specificity, affinity and/or capacity. In some instances, framework residues of the human immunoglobulin are replaced by corresponding non-human residues.

A "human antibody" is one that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues.

An "intrabody" is an antibody that is expressed within a cell and which binds to an intracellular protein. Methods of preparing intrabodies are known in the art. For example, certain methods of producing and using intrabodies are provided by the Marschall et al. reference, mAbs, 2015, 7(6):2020-1035, which is hereby incorporated by reference in its entirety.

The term "complementarity determining region" or "CDR" when used herein refers to the regions of an antibody-variable domain that are hypervariable in sequence and/or form structurally defined loops. Generally, antibodies comprise six CDRs; three in the VH (H1, H2, H3) and three in the VL (L1, L2, L3). In native antibodies, H3 and L3 display the most diversity of the six CDRs and H3 in particular is believed to play a unique role in conferring fine specificity to antibodies.

A number of CDR delineations are in use and are encompassed herein. The Kabat CDRs are based on sequence variability and are the most commonly used (Kabat et al.).

"Framework" residues are those variable-domain residues other than the CDR residues as herein defined.

As use herein, the term "specifically recognizes" refers to measurable and reproducible binding between an epitope and an antibody that is determinative of the presence of the epitope. This term may be interchanged with the terms "specifically binds", "specifically binding" and grammatical variants of these two terms. For example, the disclosed tau antibodies can specifically or preferentially bind specific tau epitopes with greater affinity, avidity, more readily and/or with greater duration than it binds to other epitopes. An antibody that specifically or preferentially binds to a first epitope may or may not specifically or preferentially bind to a second epitope. As such, "specific recognition" does not necessarily require (although it can include) exclusive recognition. An antibody specifically binding to an antigen has the equilibrium dissociation constant ($K_D$) of lower than about $10^{-6}$ M, lower than about $10^{-9}$ M, or lower than about $10^{-12}$ M for the binding between the antibody and the corresponding antigen.

On the other hand, "non-specific binding" refers to the binding that is not based on specific interactions between an antibody and its corresponding antigen. Non-specific binding may result from non-specific interactions, such as, Van Der Waals forces. $K_D$ for the binding between the antibody and a non-specific antigen is typically higher than about $10^{-5}$ M, higher than about $10^{-4}$ M or higher than about $10^{-2}$ M.

Antibody "effector functions" refer to those biological activities attributable to the Fc region (a native sequence Fc region or amino acid sequence variant Fc region) of an antibody and vary with the antibody isotype.

The term "Fc region" herein is used to define a C-terminal region of an immunoglobulin heavy chain, including native-sequence Fc regions and variant Fc regions. The boundaries of the Fc region of antibodies of different classes and subclasses are known in the art.

As used herein, "percent (%) amino acid sequence identity" and "homology" with respect to a sequence refers to the percentage of amino acid residues in a candidate sequence that are identical with the amino acid residues in the reference sequence. The sequence identity can be determined by the sequence alignment programs that are well known in the art. Non-limiting examples of such sequence alignment programs include, but are by not limited to, TBLASTN, BLASTP, FASTA, TFASTA and CLUSTALW (Pearson and Lipman, 1988, *Proc. Natl. Acad. Sci. USA* 85(8):2444-2448; Altschul et al., 1990, *J. Mol. Biol.* 215(3):403-410; Thompson et al., 1994, *Nucleic Acids Res.* 22(2):4673-4680; Higgins et al., 1996, *Methods Enzymol.* 266:383-402; Altschul et al., 1990, *J. Mol. Biol.* 215(3):403-410; Altschul et al., 1993, *Nature Genetics* 3:266-272). Sequence comparisons are, typically, conducted using default parameters provided by the vendor or using those parameters set forth in the above-identified references, which are hereby incorporated by reference in their entireties.

The term "vector" as used herein, is intended to refer to a nucleic acid molecule capable of transporting another nucleic acid to which it has been linked. One type of vector is a "plasmid", which refers to a circular double stranded DNA into which additional DNA segments may be ligated. Other vectors include a viral vector, such as a phage vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell and thereby are replicated along with the host genome. Moreover, certain vectors are capable of directing the expression of genes to which they are operatively linked. Such vectors are referred to herein as "expression vectors".

A "host cell" includes an individual cell or cell culture that can be or has been a recipient for vector(s) for incorporation of polynucleotide inserts. Host cells include progeny of a single host cell and the progeny may not necessarily be completely identical (in morphology or in genomic DNA complement) to the original parent cell due to natural, accidental, or deliberate mutation. A host cell includes cells transfected in vivo with a polynucleotide(s) disclosed herein.

SEQ ID NOs: 1 to 6 represent the sequences of 2N/4R, 1N/4R, 0N/4R, 2N/3R, 1N/3R and 0N/3R isoforms of human tau, respectively. Throughout this disclosure, specific residues and positions are represented with respect to SEQ ID NO: 1. If in this specification or the claims an amino acid residue is indicated by an amino acid identification code and a residue position, such description corresponds to the amino acid and the specific position within SEQ ID NO: 1. For example, recitation of "Ser199" or "S199" indicates that the identified residue corresponds to the serine residue at $199^{th}$ position in SEQ ID NO: 1. Such nomenclature applies even if a fragment of SEQ ID NO: 1 is identified. For example, the phrase "Ser199 within SEQ ID NO: 2" indicates that the identified residue corresponds to the serine residue at $199^{th}$ position in SEQ ID NO: 1 even if SEQ ID NO: 2 is shorter than SEQ ID NO: 1. Sequence alignment of SEQ ID NO: 1 with the noted sequence can be performed to identify the referenced position. Also, unless otherwise indicated, if in this specification or the claims a stretch of amino acids is indicated by residue positions, such description corresponds to the amino acid positions within SEQ ID NO: 1. For example, recitation of "amino acids 244-274" indicates that the identified stretch of amino acids corresponds to the stretch of amino acids in the relevant positions in SEQ ID NO: 1.

Tauopathies including AD and PSP are a diverse group of progressive neurodegenerative disorders pathologically defined by inclusions containing aberrantly aggregated and/or post-translationally modified tau. The tau pathology burden correlates with neurodegeneration and dementia observed in these diseases. The microtubule binding domain of tau is essential for its physiological functions in promoting neuronal cytoskeletal stability. However, it is also required for tau to assemble into an amyloid structure that comprises pathological inclusions.

Disclosed herein are antibodies that recognize the second (R2) or fourth (R4) MTBD repeat domain of tau. Thus, the disclosed antibodies can be used in the identification and differentiation between R4-repeat tau and R3-/R4-repeat tau. The antibodies disclosed herein are highly specific for tau and recognize pathological tau inclusions in human tauopathies including AD and PSP and in transgenic mouse models of tauopathies. These antibodies can be used for identifying and characterizing different tauopathies and to diagnose and treat tauopathies.

Tauopathies including AD and PSP are a diverse group of progressive neurodegenerative disorders pathologically defined by inclusions containing aberrantly aggregated, post-translationally modified tau. The tau pathology burden correlates with neurodegeneration and dementia observed in these diseases. The microtubule binding domain of tau is essential for its physiological functions in promoting neuronal cytoskeletal stability. However it is also required for tau to assemble into an amyloid structure that comprises pathological inclusions.

Also provided are monoclonal antibodies that specifically recognize the second or fourth MTBD repeat domain of tau, thus enabling the identification specifically of 4R tau versus 3R/4R tau. These antibodies are highly specific for tau and recognize pathological tau inclusions in human tauopathies including AD and PSP and in transgenic mouse models of tauopathies. The disclosed antibodies disclosed herein can be used in identifying and characterizing different tauopathies and to treat tau pathology in these diseases, for example, with an immunotherapy.

Tau antibodies or antigen binding fragments thereof disclosed herein specifically recognize tau epitopes comprising or consisting of MTBD R2 or R4. For example, in a Western blot analysis using whole brain extracts from unperfused mice, the tau antibodies or antigen binding fragments thereof disclosed herein do not specifically recognize any protein having a molecular weight of less than 37 Kd and greater than 75 Kd.

Also disclosed herein are tau antibodies and antigen binding fragments thereof that specifically recognize epitopes consisting of amino acid sequences of SEQ ID NO: 9. In certain such embodiments, the antibody or antigen binding fragment thereof comprises light chain CDR1, CDR2 and CDR3 of SEQ ID NOs: 15, 16 and 17, respectively. In further such embodiments, the antibody or antigen binding fragment thereof comprises heavy chain CDR1, CDR2 and CDR3 of SEQ ID NOs: 18, 19 and 20, respectively. In some embodiments, the disclosed antibodies or antigen binding fragments thereof specifically recognize tau epitope consisting of SEQ ID NO: 9, wherein the antibody comprises: light chain CDR1, CDR2 and CDR3 of SEQ ID NOs: 15, 16 and 17, respectively and heavy chain CDR1, CDR2 and CDR3 of SEQ ID NOs: 18, 19 and 20, respectively. For example, disclosed herein is an antibody that specifically recognizes tau epitope consisting of SEQ ID NO: 9, wherein the antibody comprises the light chain sequence of SEQ ID NO: 13 and the heavy chain sequence of SEQ ID NO: 14.

The antibodies or antigen binding fragments thereof having the light chain CDR1, CDR2 and CDR3 of SEQ ID NOs: 15, 16 and 17, respectively, the heavy chain CDR1, CDR2 and CDR3 of SEQ ID NOs: 18, 19 and 20, respectively, the light chain sequence of SEQ ID NO: 13, or the heavy chain sequence of SEQ ID NO: 14 can be the antibodies or antigen binding fragments thereof belonging to IgA, IgD, IgE, IgG or IgM.

In certain embodiments, the disclosed antibodies or antigen binding fragments thereof specifically recognize tau epitopes consisting of amino acid sequences of SEQ ID NO: 11. In certain such embodiments, the antibody or antigen binding fragment thereof comprises light chain CDR1, CDR2 and CDR3 of SEQ ID NOs: 23, 24 and 25, respectively. In further such embodiments, the antibody or antigen binding fragment thereof comprises heavy chain CDR1, CDR2 and CDR3 of SEQ ID NOs: 26, 27 and 28, respectively. In some embodiments, the disclosed antibodies specifically recognize tau epitope consisting of SEQ ID NO: 11, wherein the antibody comprises: light chain CDR1, CDR2 and CDR3 of SEQ ID NOs: 23, 24 and 25, respectively and heavy chain CDR1, CDR2 and CDR3 of SEQ ID NOs: 26, 27 and 28, respectively. For example, the disclosed antibody can specifically recognizes tau epitope consisting of SEQ ID NO: 11, wherein the antibody comprises the light chain sequence of SEQ ID NO: 21 and the heavy chain sequence of SEQ ID NO: 22.

The antibodies or antigen binding fragments thereof having the light chain CDR1, CDR2 and CDR3 of SEQ ID NOs: 23, 24 and 25, respectively, the heavy chain CDR1, CDR2 and CDR3 of SEQ ID NOs: 26, 27 and 28, respectively, the light chain sequence of SEQ ID NO: 21, or the heavy chain sequence of SEQ ID NO: 22 can be the antibodies or antigen binding fragments thereof belonging to IgA, IgD, IgE, IgG or IgM.

In some embodiments, the disclosed antibodies or antigen binding fragments thereof specifically recognize tau epitope consisting of SEQ ID NO: 11. In certain such embodiments, the antibody or antigen binding fragment thereof comprises light chain CDR1, CDR2 and CDR3 of SEQ ID NOs: 31, 32 and 33, respectively. In further such embodiments, the antibody or antigen binding fragment thereof comprises heavy chain CDR1, CDR2 and CDR3 of SEQ ID NOs: 34, 35 and 36, respectively. In some embodiments, the disclosed antibodies specifically recognize tau epitope consisting of SEQ ID NO: 11, wherein the antibody comprises: light chain CDR1, CDR2 and CDR3 of SEQ ID NOs: 31, 32 and 33, respectively and heavy chain CDR1, CDR2 and CDR3 of SEQ ID NOs: 34, 35 and 36, respectively. For example, disclosed herein is an antibody that specifically recognizes tau epitope consisting of SEQ ID NO: 11, wherein the antibody comprises the light chain sequence of SEQ ID NO: 29 and the heavy chain sequence of SEQ ID NO: 30.

The antibodies or antigen binding fragments thereof having the light chain CDR1, CDR2 and CDR3 of SEQ ID NOs: 31, 32 and 33, respectively, the heavy chain CDR1, CDR2 and CDR3 of SEQ ID NOs: 34, 35 and 36, respectively, the light chain sequence of SEQ ID NO: 29, or the heavy chain sequence of SEQ ID NO: 30 can be the antibodies or antigen binding fragments thereof belonging to IgA, IgD, IgE, IgG or IgM.

In some embodiments, the antibody or antigen binding fragment thereof comprises light chain CDR1, CDR2 and CDR3 of SEQ ID NOs: 40, 41 and 42, respectively. In further such embodiments, the antibody or antigen binding fragment thereof comprises heavy chain CDR1, CDR2 and CDR3 of SEQ ID NOs: 43, 44 and 45, respectively. In some embodiments, the disclosed antibodies that specifically recognize tau epitope consisting of SEQ ID NO: 11, comprises: light chain CDR1, CDR2 and CDR3 of SEQ ID NOs: 40, 41 and 42, respectively and heavy chain CDR1, CDR2 and CDR3 of SEQ ID NOs: 43, 44 and 45, respectively. For example, the disclosed antibody can comprise the light chain sequence of SEQ ID NO: 38 and the heavy chain sequence of SEQ ID NO: 39.

The antibodies or antigen binding fragments thereof having the light chain CDR1, CDR2 and CDR3 of SEQ ID NOs: 40, 41 and 42, respectively, the heavy chain CDR1, CDR2 and CDR3 of SEQ ID NOs: 43, 44 and 45, respectively, the light chain sequence of SEQ ID NO: 38, or the heavy chain sequence of SEQ ID NO: 39 can be the antibodies or antigen binding fragments thereof belonging to IgA, IgD, IgE, IgG or IgM.

In some embodiments, the disclosed tau antibodies or antigen binding fragments thereof comprise a light chain domain having an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO: 13, 21, 29 or 38. In specific embodiments, the disclosed tau antibodies or antigen binding fragments thereof do not have any amino acid variants in the CDR sequences of SEQ ID NO: 15-17, 23-25, 31-33 or 40-42 respectively.

In some embodiments, the disclosed tau antibodies or antigen binding fragments thereof comprise a heavy chain variable domain comprising an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO: 14, 22, 30 or 39. In specific embodiments, the disclosed tau antibodies or antigen binding fragments thereof do not have any amino acid variants in the CDR sequences of SEQ ID NO: 18-20, 26-28, 34-36 or 43-45 respectively.

Disclosed herein are tau antibodies or antigen binding fragments thereof, comprising: a light chain variable domain and/or a heavy chain variable domain, wherein the light chain variable domain comprises the CDRs of a light chain variable domain of a monoclonal antibody selected from 81A11, 83E4, 94-3A2, 94-3A2-2, 94-3A6 and 94-4F1 and/or the heavy chain variable domain comprises the CDRs of a heavy chain variable domain of a monoclonal antibody selected from 81A11, 83E4, 94-3A2, 94-3A2-2, 94-3A6 and 94-4F1.

Disclosed herein are tau antibodies or antigen binding fragments thereof, comprising: a light chain variable domain and a heavy chain variable domain, wherein the light chain variable domain comprises the CDRs of a light chain variable domain of a monoclonal antibody selected from 81A11, 83E4, 94-3A2, 94-3A2-2, 94-3A6 and 94-4F1 and the heavy chain variable domain comprises the CDRs of a heavy chain variable domain of a monoclonal antibody selected from 81A11, 83E4, 94-3A2, 94-3A2-2, 94-3A6 and 94-4F1.

In further such embodiments, tau antibodies or antigen binding fragments thereof, comprise: a light chain variable domain and/or a heavy chain variable domain, wherein the light chain variable domain comprises the CDRs of a light chain variable domain of a monoclonal antibody selected from 83E4, 94-3A2, 94-3A2-2, 94-3A6 and 94-4F1 and/or the heavy chain variable domain comprises the CDRs of a heavy chain variable domain of a monoclonal antibody selected from 83E4, 94-3A2, 94-3A2-2, 94-3A6 and 94-4F1.

In particular embodiments, tau antibodies or antigen binding fragments thereof, comprise: a light chain variable domain and/or a heavy chain variable domain, wherein the light chain variable domain comprises the CDRs of a light chain variable domain of a monoclonal antibody 81A11 and/or the heavy chain variable domain comprises the CDRs of a heavy chain variable domain of a monoclonal antibody 81A11.

Binding specificities of disclosed monoclonal antibodies are provided in Table 1 below.

TABLE 1

MTBD tau antibodies.

| Antibody | Antigen | Specificity | Isotype |
|---|---|---|---|
| 81A11 | αS 21-140/K18 | R2 | IgG1 |
| 83E4 | αS 21-140/K18 | R4 | IgG1 |
| 94-3A2-2 | αS 21-140/K18/Aβ1-42 | R4 | IgG2a |
| 94-3A6 | αS 21-140/K18/Aβ1-42 | R4 | IgG2b |
| 94-4F1 | αS 21-140/K18/Aβ1-42 | R4 | IgG2a |

Antibody Preparation

Tau antibodies of the present disclosure include polyclonal antibodies or monoclonal antibodies. Monoclonal antibodies can be murine monoclonal antibodies, human monoclonal antibodies, humanized antibodies, chimeric antibodies, human antibodies, antibody fragments (e.g., Fab, Fab'-SH, Fv, scFv and F(ab')$_2$ fragments), antibodies having modified effector functions, fusion proteins containing an antibody portion, glycosylation variants of antibodies, amino acid sequence variants of antibodies, covalently modified antibodies and any other modified configuration of a protein that includes an epitope recognition site, such as an epitope consisting of amino acid sequence of SEQ ID NO: 9 or 11. The tau antibodies can be human, murine, rat, or of any other origin (including chimeric or humanized antibodies).

Polyclonal tau antibodies are generally raised in animals by multiple subcutaneous (sc) or intraperitoneal (ip) injections of the relevant epitopes and an adjuvant. The relevant epitope can be conjugated to a protein that is immunogenic in the species to be immunized. Examples of such proteins include KLH, serum albumin, bovine thyroglobulin, or soybean trypsin inhibitor. Such conjugation can be performed using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, SOCl$_2$, or R$_1$N═C═NR, where R and R$_1$ are independently lower alkyl groups. Examples of adjuvants which may be employed include Freund's complete adjuvant and MPL-TDM adjuvant (monophosphoryl Lipid A, synthetic trehalose dicorynomycolate). Conjugates also can be made in recombinant-cell culture as protein fusions. Appropriate immunization protocols are known to a skilled artisan and such embodiments are within the purview of the disclosed compositions and methods.

The animals can be immunized against the desired antigen, immunogenic conjugates, or derivatives by combining appropriate amounts of epitopes or epitope conjugates (e.g., 100 µg for rabbits or 5 µg for mice) with appropriate amount (e.g., 3 times the weight) of Freund's complete adjuvant and injecting the solution intradermally at multiple sites. Also, aggregating agents such as alum are suitable to enhance the immune response. After an appropriate duration of time, such as about one month, the animals can be boosted with about one-fifth or one-tenth of the original amount of peptide or conjugate in Freund's complete adjuvant by subcutaneous injection at multiple sites. Seven to fourteen days later, the animals can be bled and the serum can be assayed for antibody titer. Animals can be further boosted with the epitope until the antibody titer plateaus.

Monoclonal tau antibodies are a population of substantially homogeneous antibodies, i.e., the individual antibodies comprising the population are identical except for possible naturally occurring mutations and/or post-translational modifications (e.g., isomerizations, amidations) that may be present in minor amounts. Thus, "monoclonal antibodies" do not comprise a mixture of discrete antibodies. For example, the monoclonal tau antibodies can be made using the hybridoma method described by Kohler et al., Nature, 256:495 (1975), or may be made by recombinant DNA methods (U.S. Pat. No. 4,816,567). Methods of producing hybridoma cell lines producing antibodies of interest are well known in the art and such embodiments are within the purview of the disclosed compositions and methods.

Monoclonal antibodies that specifically recognize tau epitopes can also be made by recombinant DNA methods, such as those disclosed in U.S. Pat. No. 4,816,567. DNA encoding the monoclonal antibodies is isolated and sequenced using conventional procedures (e.g., by using oligonucleotide probes that specifically bind to genes encoding the heavy and light chains of murine antibodies). The hybridoma cells can serve as a source of such DNA. To synthesize monoclonal antibodies, the isolated DNA can be placed into expression vectors, which are then transfected into host-cells such as *Escherichia coli* cells, simian COS cells, Chinese hamster ovary (CHO) cells, or myeloma cells that do not otherwise produce an antibody. Methods of expressing antibodies in host cells of interest are known in the art and such embodiments are within the purview of the disclosed compositions and methods.

In certain embodiments, tau antibodies can be isolated from antibody phage libraries. Methods of generating monoclonal antibodies using phage libraries are known in the art and such embodiments are within the purview of the disclosed compositions and methods.

The DNA encoding antibodies or fragments thereof may be modified, for example, by substituting the coding sequence for human heavy- and light-chain constant domains in place of the homologous murine sequences. Certain examples of such techniques are described in U.S. Pat. No. 4,816,567; Morrison, et al., Proc. Natl Acad. Sci. USA, 81:6851 (1984). The DNA encoding antibodies or fragments thereof may also be covalently joined the coding sequence for a non-antibody polypeptide. Typically such non-antibody polypeptides are substituted for the constant domains of an antibody. Alternatively, the constant domains of antibodies can be substituted for the variable domains of antibodies having different epitope specificity to create a chimeric bivalent antibody comprising multiple antigen binding sites having multiple and different specificity.

The monoclonal antibodies described herein can be monovalent, the preparation of which is well known in the art, for example, recombinant expression of antibody light chain and a modified heavy chain. The heavy chain is truncated generally at any point in the Fc region to prevent heavy chain crosslinking. Alternatively, the relevant cysteine residues may be substituted with another amino acid residue or are deleted to prevent crosslinking. In vitro methods are also suitable for preparing monovalent antibodies. Digestion of antibodies to produce fragments thereof, particularly Fab fragments, can be accomplished using techniques known in the art.

Chimeric or hybrid tau antibodies also may be prepared in vitro using known methods in the art, for example, using crosslinking agents. For example, immunotoxins may be constructed using a disulfide-exchange reaction or by forming a thioether bond. Examples of suitable reagents for this purpose include iminothiolate and methyl-4-mercaptobutyrimidate.

Humanized Antibodies

The disclosed Tau antibodies or antibody fragments thereof can further include humanized or human antibodies. Humanized antibodies are recombinant antibodies or antigen binding fragments thereof that contain minimal sequence derived from non-human antibodies. Humanized antibodies include human antibodies (recipient antibodies) in which CDRs of the human (recipient) antibodies are replaced by CDRs of a non-human species (donor antibody) such as mouse, rat, or rabbit having the desired specificity, affinity and capacity. Various methods of making humanized antibodies are known in the art, see for example, U.S. Pat. Nos. 5,530,101; 5,994,510; and 7,566,771, each of which is hereby incorporated by reference in its entirety. In some instances, Fv framework residues of the human antibodies are replaced by corresponding non-human portions. Humanized antibodies may also comprise residues which are found neither in the recipient antibody nor in the imported CDRs or framework sequences. In general, the humanized antibodies comprise substantially all of at least one and typically two, variable domains, in which all or substantially all of the CDRs correspond to those of the non-human antibodies and all or substantially all of the FR regions are those of the human antibodies. The humanized antibodies can also comprise at least a portion of the Fc region, typically of a human Fc. As such, humanized antibodies are chimeric antibodies (U.S. Pat. No. 4,816,567).

In some embodiments, the tau antibody is a chimeric antibody comprising the heavy and light chain variable domains of any of the tau antibodies described herein (e.g., antibodies 81A11, 83E4, 94-3A2, 94-3A2-2, 94-3A6 and 94-4F1) and constant regions from a human antibody.

The choice of human variable domains, both light and heavy, to be used in making the humanized antibodies dictates antigenicity of the humanized antibodies in humans. Typically, the sequence of the variable domain of a rodent antibody is screened against the entire library of known human variable-domain sequences. The human sequence which is closest to that of the rodent is then accepted as the human framework for the humanized antibody. Sims et al., J. Immunol., 151:2296 (1993); Chothia et al., J. Mol. Biol., 196:901 (1987). Alternatively, a particular framework derived from the consensus sequence of all human antibodies of a particular subgroup of light or heavy chains can be used. The same framework may be used for several different humanized antibodies. Carter et al., Proc. Nat'l Acad. Sci. USA 89:4285 (1992); Presta et al., J. Immunol. 151:2623 (1993).

Furthermore, humanized antibodies are designed to retain high affinity for the epitope and other favorable biological properties. To that end, humanized antibodies are prepared by analyzing the parental sequences and various conceptual humanized products using three-dimensional models of the parental and humanized sequences. Three-dimensional antibody models are commonly available and are familiar to those skilled in the art. Software programs can be used to illustrate and display probable three-dimensional conformational structures of selected candidate antibodies. These displays can be analyzed to identify the likely roles of the residues in the functioning of the candidate antibody sequences. In this way, framework residues can be selected and combined from the recipient and import sequences so that the desired antibody characteristic, such as increased affinity for the target epitope is achieved. In general, the CDRs are involved in influencing antigen binding.

Various forms of the humanized tau antibody are contemplated. For example, the humanized tau antibody may be an antibody fragment, such as a Fab, which is optionally conjugated with one or more agents to generate an immunoconjugate. Alternatively, the humanized tau antibody may be an intact antibody, such as an intact IgG1 antibody.

Human Antibodies

Alternatively, human tau antibodies can be generated. For example, transgenic animals (e.g., mice) can be produced that are capable, upon immunization, of producing a full repertoire of human antibodies in the absence of endogenous antibody production. The homozygous deletion of the antibody heavy-chain joining region ($J_H$) gene in chimeric and germ-line mutant mice results in complete inhibition of endogenous antibody production. Transfer of the human germ-line antibody gene array in such germ-line mutant mice results in the production of human antibodies upon immunization with an epitope. Methods of producing and using such genetically engineered mice to produce human antibodies are known in the art and such embodiments are within the purview of the disclosed compositions and methods.

Alternatively, phage display technology can be used to produce human tau antibodies and antibody fragments thereof in vitro, from antibody variable (V) domain gene repertoires from unimmunized donors. Phage display technology is known in the art and described by, for example, McCafferty et al., Nature 348:552-553 (1990); Hoogenboom and Winter, J. Mol. Biol. 227: 381 (1991).

In other embodiments, ribosome display technology can be used to produce human tau antibodies and antibody fragments in vitro (e.g., Roberts and Szostak (1997) Proc Natl Acad Sci 94:12297-12302; Schaffitzel et al. (1999) J. Immunolical Methods 231:119-135; Lipovsek and Pluckthun (2004) J. Immunological Methods 290:51-67).

The techniques of Cole et al. and Boerner et al. are also available for the preparation of human tau monoclonal antibodies (Cole et al., Monoclonal Antibodies and Cancer Therapy, Alan R. Liss, p. 77 (1985) and Boerner et al., J. Immunol. 147(1): 86-95 (1991). Similarly, human tau antibodies can be made by introducing human antibody loci into transgenic animals, e.g., mice in which the endogenous antibody genes have been partially or completely inactivated. Upon challenge, human antibody production is observed, which closely resembles that seen in humans in all respects, including gene rearrangement, assembly and antibody repertoire. Certain such techniques are described, for example, in U.S. Pat. Nos. 5,545,807; 5,545,806, 5,569,825, 5,625,126, 5,633,425, 5,661,016 and in the following publications: Marks et al., Bio/Technology 10: 779-783 (1992); Lonberg et al., Nature 368: 856-859 (1994); Morrison, Nature 368: 812-13 (1994), Fishwild et al., Nature Biotechnology 14: 845-51 (1996), Neuberger, Nature Biotechnology 14: 826 (1996) and Lonberg and Huszar, Intern. Rev. Immunol. 13: 65-93 (1995).

Finally, human tau antibodies may also be generated in vitro by activated B-cells (see U.S. Pat. Nos. 5,567,610 and 5,229,275).

Intrabodies

Typically, intrabodies are expressed within a target cell. Such expression can be accomplished by introduction into a target cell of a gene encoding an intrabody. Intrabodies can also be modified for intracellular localization when produced in cells other than target cells, such as prokaryotes or other suitable host cells. Intrabodies can remain in the cytoplasm. Intrabodies can also be introduced into the nucleii of target cells, for example, via a nuclear localization signal. Intrabodies can also undergo cotranslational translocation across the membrane into the lumen of the endoplasmic reticulum (ER). Translation and retention of intrabodies into the ER can be facilitated by a peptide sequence, for example, tetrapeptide Lys-Asp-Glu-Leu (SEQ ID NO: 37), which prevents the intrabody from being secreted from the ER. Stability and structure of intrabodies can be increased by one or more techniques selected from the use of scFvs, modification of immunoglobulin VL domains for hyperstability, selection of antibodies resistant to the more reducing intracellular environment and expression as a fusion protein, for example, with a maltose binding protein or other stable intracellular proteins.

Antibody Fragments

Using tau antibody fragments, rather than whole tau antibodies, provides certain advantages, such as rapid clearance attributable to small sizes. Various techniques can be used for producing antibody fragments. The fragments can be derived by proteolytic digestion of intact antibodies (see, e.g., Morimoto et al., J. Biochem. Biophys. Method. 24:107-117 (1992); and Brennan et al., Science 229:81 (1985)). Alternatively, the fragments can be produced by recombinant host-cells, for example, using nucleic acids encoding fragments of tau antibodies of the present disclosure. Fab, Fv and scFv antibody fragments can all be expressed in and secreted from *E. coli*, thus allowing the straightforward production of large amounts of these fragments. Fragments of tau antibodies can also be isolated from the antibody phage libraries as discussed above. Alternatively, Fab'-SH fragments can be directly recovered from *E. coli* and chemically coupled to form F(ab')$_2$ fragments (Carter et al., Bio/Technology 10:163-167 (1992)). F(ab')$_2$ fragments can also be isolated from recombinant host-cell culture. Production of Fab and F(ab')$_2$ antibody fragments with increased in vivo half-lives are described in U.S. Pat. No. 5,869,046. In other embodiments, the antibody of choice is a single chain Fv fragment (scFv). See WO 93/16185; U.S. Pat. Nos. 5,571,894 and 5,587,458. The tau antibody fragment may also be a "linear antibody", e.g., as described in U.S. Pat. No. 5,641,870. Such linear antibody fragments may be monospecific or bispecific.

Effector Function Engineering

It may also be desirable to modify the disclosed tau antibodies to modify effector function and/or to increase serum half-life of the antibody. For example, the Fc receptor binding site on the constant region may be modified or mutated to remove or reduce binding affinity to certain Fc receptors, such as FcgRI, FcgRII and/or FcgRIII. In some embodiments, the effector function is impaired by removing N-glycosylation of the Fc region (e.g., in the CH2 domain of IgG) of the antibody. In some embodiments, the effector function is impaired by modifying regions such as 233-236, 297 and/or 327-331 of human IgG as described in PCT WO 99/58572 and Armour et al., Molecular Immunology 40: 585-593 (2003); Reddy et al., J. Immunology 164:1925-1933 (2000).

The constant region of the tau antibodies described herein may also be modified to impair complement activation. For example, complement activation of IgG antibodies following binding of the C1 component of complement may be reduced by mutating amino acid residues in the constant region in a C1 binding motif (e.g., C1q binding motif). Ala mutation for each of D270, K322, P329, P331 of human IgG1 significantly reduced the ability of the antibody to activate complement. For murine IgG2b, C1q binding motif constitutes residues E318, K320 and K322. Idusogie et al. (2000) J. Immunology 164:4178-4184; Duncan et al. (1988) Nature 322: 738-740. As the C1s binding motif E318, K320 and K322 identified for murine IgG2b is believed to be common for other antibody isotypes (Duncan et al. (1988) Nature 322:738-740), C1q binding activity for IgG2b can be abolished by replacing any one of the three specified residues with a residue having an inappropriate functionality on its side chain. It is not necessary to replace the ionic residues only with Ala to abolish C1q binding. It is also possible to use other alkyl-substituted non-ionic residues, such as Gly, Ile, Leu, or Val, or such aromatic non-polar residues as Phe, Tyr, Trp and Pro in place of any one of the three residues in order to abolish C1q binding. In addition, it is also possible to use such polar non-ionic residues as Ser, Thr, Cys and Met in place of residues 320 and 322, but not 318, to abolish C1s binding activity. In addition, removal of carbohydrate modifications of the Fc region necessary for complement binding can prevent complement activation Glycosylation of a conserved asparagine (Asn-297) on the CH2 domain of IgG heavy chains is essential for antibody effector functions (Jefferis et al. (1998) Immunol Rev 163:59-76). Modification of the Fc glycan alters IgG conformation and reduces the Fc affinity for binding of complement protein C1q and effector cell receptor FcR (Alhorn et al. (2008) PLoS ONE 2008; 3:e1413). Complete removal of the Fc glycan abolishes CDC and ADCC. Deglycosylation can be performed using glycosidase enzymes for example Endoglycosidase S (EndoS), 108 kDa enzyme encoded by the gene endoS of *Streptococcus pyogenes* that selectively digests asparagine-linked glycans on the heavy chain of all IgG subclasses, without action on other antibody classes or other glycoproteins (Collin et al. (2001) EMBO J 2001; 20:3046-3055).

To increase the serum half-life of the antibody, a salvage receptor binding epitope can be incorporated into the antibody (especially an antibody fragment) as described in U.S. Pat. No. 5,739,277. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

Tau antibodies of the present disclosure, or antibody fragments thereof, can be further modified to contain additional non-proteinaceous moieties that are known in the art and readily available. In some embodiments, the moieties suitable for derivatization of the antibody are water-soluble polymers. Non-limiting examples of water-soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers) and dextran or poly (n-vinyl pyrrolidone)polyethylene glycol, polypropylene glycol homopolymers, polypropylene oxide/ethylene oxide co-polymers, polyoxyethylated polyols (e.g., glycerol), polyvinyl alcohol and mixtures thereof. Polyethylene glycol propionaldehyde may have advantages in manufacturing due to its stability in water. The polymer may be of any molecular weight and may be branched or unbranched. The number of polymers attached to the antibody may vary and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc. Such techniques and other suitable formulations are disclosed in Remington: The Science and Practice of Pharmacy, 20th Ed., Alfonso Gennaro, Ed., Philadelphia College of Pharmacy and Science (2000).

In further embodiments, tau antibodies or antigen binding fragments thereof can be conjugated to a label, for example, an enzyme label, a radioisotope label, a fluorescent label, or a bioluminescent label. The labels are typically used for detection and visualization of antigen-antibody complex. Non-limiting examples of the enzyme labels are horseradish peroxidase label, alkaline phosphatase, β-galactosidase, luciferase, acetylcholine esterase and glucose oxidase. Additional examples of enzymes appropriate for labeling antibodies for detection and visualization of antigen-antibody complex are well known to a person of ordinary skill in the art and such embodiments are within the purview of the disclosed compositions and methods. Non-limiting examples of radioisotope labels are $^{125}I$, $^{35}S$, $^{14}C$, $^{32}P$ and $^{3}H$. Additional examples of radiolabels appropriate for labeling antibodies for detection and visualization of antigen-antibody complex are well known to a person of ordinary skill in the art and such embodiments are within the purview of the disclosed compositions and methods. Non-limiting examples of fluorescent labels are umbelliferone, fluorescein, rhodamine, dichlorotriazinylamine fluorescein, dansyl chloride, fluorescein isothiocyante (FITC), phycoerythrin (PE), Cy5-phycoerythrin (Cy5-PE), Cy7-phycoerythrin (Cy7-PE), allophycocyanin (APC), Cy7-allophycocyanin (Cy7-APC), texas red (TR) and cascade blue. Additional examples of fluorescent labels appropriate for labeling antibodies for detection and visualization of antigen-antibody complex are well known to a person of ordinary skill in the art and such embodiments are within the purview of the disclosed compositions and methods invention. Non-limiting examples of bioluminescent labels are photoprotein aequorin, adenosine triphosphate, nicotinamide adenine dinucleotide and D-luciferin. Additional examples of bioluminescent labels appropriate for labeling antibodies for detection and visualization of antigen-antibody complex are well known to a person of ordinary skill in the art and such embodiments are within the purview of the disclosed compositions and methods.

A further embodiment of the disclosed compositions and methods is a kit comprising an antibody or antigen binding fragment thereof. The kit can contain the antibody along with additional reagents required for processing of a sample for the immunoassay, reagents for conducting the immunoassay and instructional materials and manuals for performing the immunoassay.

As noted above, the tau antibodies and the antigen binding fragments thereof disclosed herein could be used for treating or preventing tauopathies. Accordingly, also disclosed herein are methods of treating or preventing a tauopathy in a subject, comprising administering to the subject a therapeutically effective amount of tau antibodies or the antigen binding fragments thereof disclosed herein. Non-limiting examples of tauopathies that can be treated according to the disclosed methods include AD, chronic traumatic encephalopathy, corticobasal degeneration, frontotemporal labor degeneration, Pick disease, or PSP.

Tau antibodies and the antigen binding fragments thereof disclosed herein when used for treating or preventing tauopathies are administered to subjects in the form of pharmaceutical compositions. Accordingly, also disclosed herein are pharmaceutical compositions comprising tau antibodies or antigen binding fragments thereof.

Tau antibodies and the antigen binding fragments thereof disclosed herein also have diagnostic utility. Therefore methods of using the antibodies or antigen binding fragments thereof for diagnostic purposes as the detection of tau in a subject or in tissue samples derived from a subject. In some embodiments, the subject is a human. In some embodiments, the subject is suffering from a neurodegenerative disorder, particularly, a tauopathy, such as AD, chronic traumatic encephalopathy, corticobasal degeneration, frontotemporal labor degeneration, Pick disease, PSP and Parkinsonism linked to chromosome 17 with tau pathology.

The diagnostic methods of the disclosed compositions and methods involve administering tau antibodies or antigen binding fragments thereof to a subject and detecting the antibodies or antigen binding fragments thereof bound to tau protein in the subject. Binding of the tau antibodies or antigen binding fragments thereof may be quantified, for example, by non-invasive techniques such as positron emission tomography (PET), X-ray computed tomography, single-photon emission computed tomography (SPECT), computed tomography (CT) and computed axial tomography (CAT). In some embodiments, the tau antibodies or antigen binding fragments thereof are conjugated to a label suitable for an in vivo visualization and the binding of the tau antibodies or antigen binding fragments to tau protein in a subject is visualized using the detectable label. Some of the labels discussed above in connection with the labels conjugated to tau antibodies or antigen binding fragments thereof can be used in such embodiments.

In some embodiments, the diagnostic methods involve detecting tau in biological samples, such as biopsy a specimen, a tissue, or a cell. A tau antibody or an antigen binding fragment thereof disclosed herein is contacted with the biological sample and tau-bound antibody or antigen binding fragment thereof is detected. The detection method may involve quantification of the tau-bound antibody. Antibody detection in biological samples can be performed with any methods known in the art, including immunofluorescence microscopy, immunocytochemistry, immunohistochemistry, ELISA, FACS analysis or immunoprecipitation.

Also disclosed herein are methods of producing the tau antibodies or antigen binding fragments thereof as disclosed herein. Typically, a nucleotide sequence encoding a tau antibody or an antigen binding fragment thereof is incorporated into a vector. Such vector is introduced into a host cell and the host cell is cultured under conditions that are appropriate for the expression, preferably, a high level expression, of the tau antibody or the antigen binding fragment thereof encoded by the vector.

Vectors useful in the disclosed compositions and methods include plasmids, viral vectors, yeast artificial chromosomes and cosmids. Additional vectors are known in the art and such embodiments are within the purview of the disclosed compositions and methods.

Typical host cells include bacteria, such as $E.\ coli$, fungi, preferably, yeast such as *Saccharomyces cerevisiae* and eukaryotic cell culture systems, preferably, mammalian cell culture systems. Additional host cells are known in the art and such embodiments are within the purview of the disclosed compositions and methods.

Materials and Methods

Mice

Tau KO mice (Stock 007251) and tau transgenic (Tg) mice line PS19 expressing human 1N4R tau with the P301S mutation driven by the mouse prion promoter were obtained from Jackson Laboratories (Stock 008169, Bar Harbor, Me., USA). JNPL3 tau transgenic mice expressing human ON4R tau with the P301L mutation were previously described (Lewis et al.). Mice tissues for biochemical or immunohistochemical analyses were obtained from archival stocks, N=10 per genotype. B6/C3H F1 mice (N=10) (Envigo, Indianapolis, Ind., USA) were used to generate antibodies.

Production and Purification of Recombinant Tau and α-Synuclein Proteins and Recombinant Tau Fusion Proteins Recombinant proteins were expressed in *Escherichia coli* ($E.\ coli$) BL21 (DE3)/RIL (Agilent Technologies, Santa Clara, Calif.). Recombinant full-length human 2N/3R and 2N/4R tau, tau K18 fragment (corresponding to residues 244-372 relative to 2N/4R human tau with an ATG codon added at the amino-terminus) and human α-synuclein (αS) were expressed using the respective cDNA cloned into the bacterial expression plasmid pRK172 and purified. All other chimeric protein cDNAs were generated by gene synthesis conducted by Genscript (Piscataway, N.J., USA) and cloned into pET16b vector. Recombinant 21-140 human αS with an ATG codon added at the amino-terminus followed by the nucleotide sequence for residues 244-372 in 4R human tau designated αS 21-140/K18 (used to generate antibodies 81A11 and 83E4) was purified using SP column with NaCl gradient elution flowed by size exclusion column. Recombinant 21-140 human αS with an ATG codon added at the amino-terminus followed by the nucleotide sequence for residues 244-372 in 4R human tau followed by human Aβ1-42 designated αS 21-140/K18/Aβ1-42 (94-3A2, 94-3A2-2, 94-3A6 and 94-4F1 antibodies) was purified using a HiTrap Q HP column (GE Healthcare Life Sciences) followed by size exclusion chromatography. Protein concentrations were determined by bicinchoninic acid (BCA) assay (Thermo Scientific) using bovine serum albumin (BSA) as the standard.

For the generation of recombinant glutathione S-transferases (GST) tagged human MTBD R1-3 (residues 244-336 relative to ON/4R tau), R1 (residues 244-274 relative to ON/4R tau), R3 (residues 306-336 relative to ON/4R tau) and R4 (residues 337-372 relative to ON/4R tau) proteins, the corresponding cDNA sequences were amplified by PCR with the respective oligonucleotides with added BamHI and EcoRI restriction sites and cloned in these sites of bacterial expression plasmid pGEX-2T. These proteins were expressed in $E.\ coli$ BL21 (DE3)/RIL with isopropyl β-D-1-thiogalactopyranoside induction. The bacteria were lysed with 2% SDS and following the addition of SDS sample buffer equal amounts of total bacterial lysates were resolved by SDS-PAGE and analyzed by immunoblotting.

Generation of New Mouse Monoclonal Antibodies

Female B6/C3H F1 mice (N=5 per peptide) were used for immunization with synthetic peptides corresponding to the MTBD in ON/4R human tau 244-372 (K18) conjugated to 21-140 αS at the N-terminus (αS 21-140/K18) or 21-140 αS at the N-terminus plus Aβ1-42 at the C-terminus (αS 21-140/K18/Aβ1-42). Protein (100 μg) in 200 μl phosphate buffered saline (PBS) was emulsified with either 100 μl of either Freunds complete adjuvant ($1^{st}$ injection; Sigma Aldrich, St. Louis, Mo.) or Freunds incomplete adjuvant (subsequent injections; Sigma Aldrich, St. Louis, Mo.). For the first immunization, mice were injected subcutaneously. An intraperitoneal (IP) injection was administered 3 weeks later. Six weeks following the initial injection, mice were boosted with an (IP) injection of the proteins in PBS. Three days later, mice were euthanized by $CO_2$ inhalation and spleens were harvested using aseptic technique.

Mouse myeloma (Sp2/O-Ag14; ATCC, Manassas, Va.) cells were maintained in high glucose (4.5 gm/L) Dulbecco's Modified Eagle Medium (DMEM) with 10% NCTC 135 Media (Sigma Aldrich, St. Louis, Mo.), 20% hybridoma grade fetal bovine serum (FBS; Hyclone, Logan, Utah), 100 U/ml penicillin, 100 U/ml streptomycin, 2 mM L-glutamine, 0.45 mM pyruvate, 1 mM oxaloacetate and 0.2 U/ml insulin at 37° C. and 8% $CO_2$. Spleens were gently homogenized in 5% FBS/Hank's balanced salt solution (HBSS; Lonza, Walkersville, Md.). Cell suspensions were collected and centrifuged to pellet cells. The cell pellet was resuspended in red blood cell lysis buffer (Sigma Aldrich, St. Louis, Mo.) and diluted with HBSS after one minute. The cells were then washed twice by centrifuging at 100 g for 10 minutes and resuspending in HBSS. Sp2/O-Ag14 cells were also washed twice with HBSS. Five million Sp2/O-Ag14 cells were added to 50 million spleen cells and, after centrifuging at 100 g for 10 minutes onto a culture dish, fusion was induced with 50% polyethylene glycol 1450 (Sigma Aldrich, St. Louis, Mo.). After washing with HBSS, cells were incubated in Sp2/O-Ag14 media at 37° C. with 8% $CO_2$ overnight. The next day, the cells were gently detached from the plate and distributed into 96 well plates with Sp2/O-Ag14 media/0.5% hybridoma enhancing supplement (Sigma Aldrich, St. Louis, Mo.)/HAT selection supplement (Sigma Aldrich, St. Louis, Mo.).

Hybridoma Screening

All hybridoma clones were screened for reactivity to K18 by enzyme-linked immunosorbent assay (ELISA). MaxiSorp plates (Thermo Scientific, Waltham, Mass.) or Immulon 4HBX plates (ThermoFisher Scientific, Waltham, Mass.) were coated with 1 μg/ml human recombinant tau or αS proteins or Aβ in PBS or 100 mM sodium bicarbonate and blocked with 5% FBS/PBS or 1% Block ACE in PBS. Media from the hybridomas were applied to plates, which were then incubated at room temperature for 3 hours. Next, the plates were washed with PBS and incubated with goat anti-mouse secondary antibody conjugated to horse radish peroxidase (HRP; Jackson Immuno Research Labs, West Grove, Pa.) for 1 hour at room temperature. Then, plates were washed and TMB substrates (Pierce, Rockford, Ill.) were applied until color changes were observed. Reactions were then quenched with 1M HCl or 85% 0-Phosphoric acid and absorbance was measured at 450 nm. Clones that were positive by ELISA were transferred to larger culture plates as needed. Antibody clones were isotyped with the mouse monoclonal antibody isotyping kit purchased from Sigma-Aldrich (St. Louis, Mo.).

Preparation of total mouse brain protein lysates Tau KO, PS19 Tg or NTg mice were euthanized by $CO_2$ inhalation and the brains were harvested. Brain tissue was homogenized in 2% SDS/50 mM Tris, pH 7.5 using a probe sonicator and then incubated for 10 min at 100° C. Protein concentrations were determined by BCA assay using BSA as the standard. Sample buffer was added and equal amounts of protein (10 µg) were resolved by SDS-PAGE and analyzed by immunoblot.

Preparation of Sarkosyl-Insoluble Human Temporal Cortex

Frozen human brain tissue was obtained a human brain tissue bank. Pulverized temporal cortex tissues from human control (n=2) or AD cases (n=3) were homogenized in high-salt (HS) buffer (50 mM Tris-HCl, pH 7.5, 0.75 M NaCl, 2 mM EDTA, 50 mM NaF with protease inhibitor cocktail [Roche]) at 3 ml buffer/g tissue and centrifuged at 100,000 g at 4° C. for 30 minutes. Supernatants were collected (HS fraction) and pellets were resuspended in HS buffer containing 1% Triton X-100 at 2 ml buffer/g tissue. Samples were centrifuged at 100,000 g at 4° C. for 30 minutes and the supernatants were collected (HS/Triton-soluble fraction). Pellets were washed in the same buffer and then re-suspended in HS buffer containing 1% sarkosyl at 1 ml buffer/g tissue and incubated at 37° C. for 30 minutes and centrifuged at 100,000 g at 4° C. for 30 minutes and supernatants were collected (sarkosyl-soluble fraction). The detergent-insoluble pellets were extracted in 0.5 ml of 4 M urea, 2% SDS, 25 mM Tris-HCl pH 7.6/g tissue, sonicated and sedimented at 100,000 g for 30 minutes at 25° C. Protein concentrations were determined by BCA assay (Thermo Scientific) using BSA as the standard. SDS sample buffer was added and equal amounts of protein (10 µg) were resolved by SDS-PAGE and analyzed by immunoblot.

Immunoblotting

Protein samples were resolved by electrophoresis on 4-12% Bis-Tris precast gels (Biorad, Hercules, Calif., USA), then electrophoretically transferred to PVDF membranes. Membranes were blocked with 0.5% casein in TBS then incubated overnight at 4° C. with primary antibodies diluted in 0.5% casein in TBS. Goat Anti-GST antibody was obtained from GE Healthcare Biosciences (Pittsburgh, Pa., USA). Following washing, blots were incubated with fluorophore-conjugated secondary antibodies diluted in 0.5% casein in TBS for 1 hour. Following washing, protein bands were visualized and quantified using an Odyssey infrared imaging and analysis system (Li-Cor Biosciences, Lincoln, Nebr., USA).

Immunohistochemistry

Paraffin embedded tissues from JNPL3 tau transgenic, PS19 tau-transgenic and non-transgenic (NTg) mice were used. All paraffin embedded, formalin fixed human brain tissues from de-identified donors were obtained through a human brain tissue bank. Sequential tissue sections were deparaffinized with xylenes and sequentially rehydrated with graded ethanol solutions (100-70%). Antigen retrieval was performed by incubating sections in a steam bath for 30 minutes. Endogenous peroxidase activity was quenched with 1.5% hydrogen peroxide/0.005% Triton-X-100/Tris-buffered Saline (TBS) for 20 minutes. Sections were blocked with 2.5% horse serum then incubated overnight at 4° C. with primary antibody. Following washing with TBS, sections were incubated with Vector ImmPress anti-mouse IgG peroxidase (Vector Laboratories, Burlingame, Calif., USA) for 30 minutes. Sections were washed with TBS and then developed with 3, 3'diaminobenzidine (DAB kit; Vector Laboratories). Reactions were stopped by immersing the slides in TBS and sections were counterstained with Mayer's hematoxylin (Sigma Aldrich, St. Louis, Mo.). Next, sections were dehydrated with an ascending series of ethanol solutions (70%-100%) followed by xylenes and coverslipped using cytoseal (Thermo Scientific, Waltham, Mass.).

All patents, patent applications, provisional applications and publications referred to or cited herein are incorporated by reference in their entirety, including all figures and tables, to the extent they are not inconsistent with the explicit teachings of this specification.

Following are examples which illustrate procedures for practicing the disclosed compositions and methods. These examples should not be construed as limiting. All percentages are by weight and all solvent mixture proportions are by volume unless otherwise noted.

A number of embodiments of the invention have been described. Nevertheless, it will be understood that various modifications may be made without departing from the spirit and scope of the disclosed compositions and methods. Accordingly, other embodiments are within the scope of the following claims.

EXAMPLES

Figures 1D, 1E, 1F:
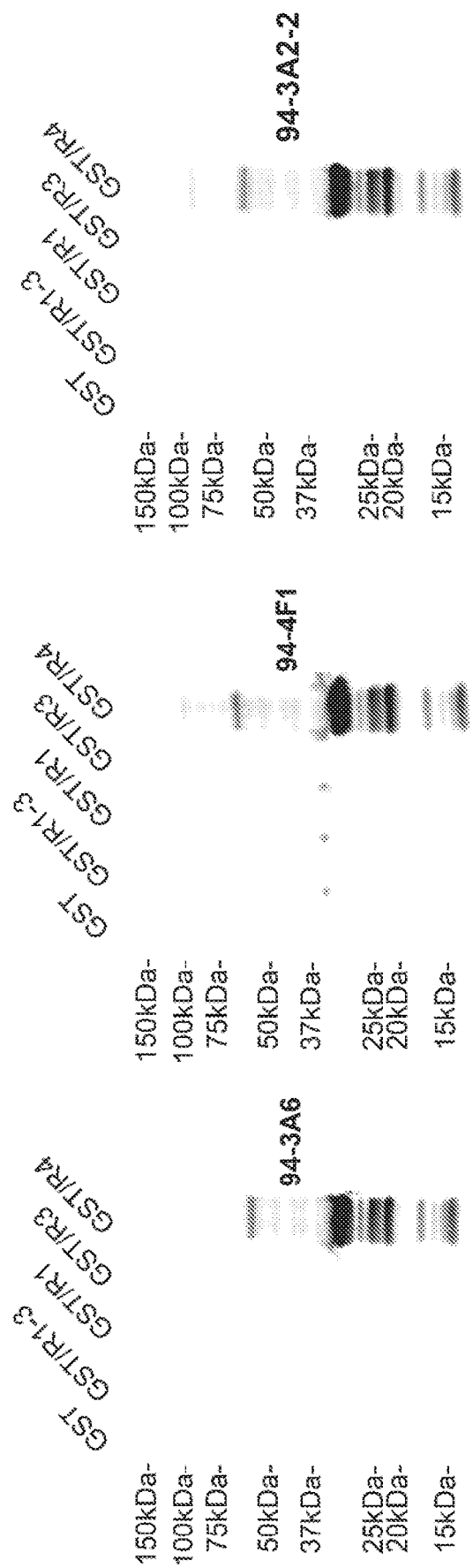
Figures 2A, 2B, 2C:
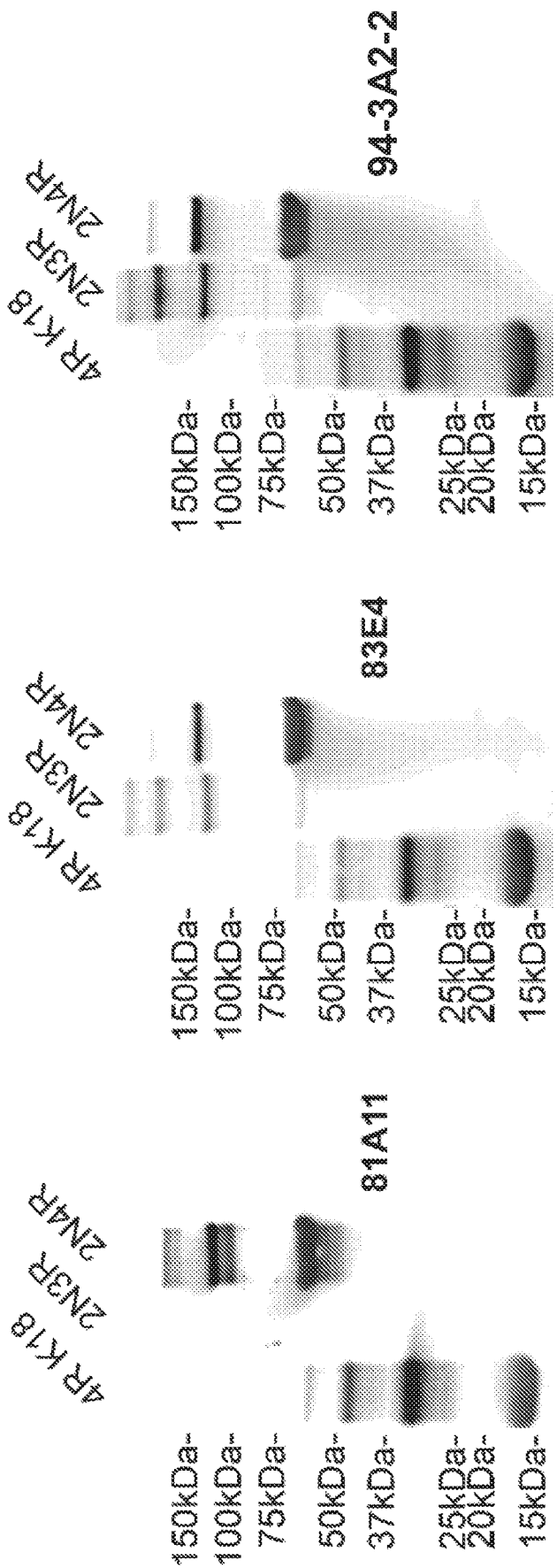
FIGS. 2A to 2E show specificity of the disclosed tau antibodies to recombinant 3-repeat and 4-repeat human tau proteins. Immunoblots of recombinant K18 tau fragment (4R microtubule binding domain) and full-length human 2N/3R and 2N/4R tau were probed with the disclosed tau antibodies 81A11 (FIG. 2A), 83E4 (FIG. 2B), 94-3A2-2 (FIG. 2C), 94-3A6 (FIG. 2D), and 94-4F1 (FIG. 2E) to determine specificity for 3R and 4R tau. The mobilities of molecular mass markers are shown on the left.
Figures 2D, 2E:
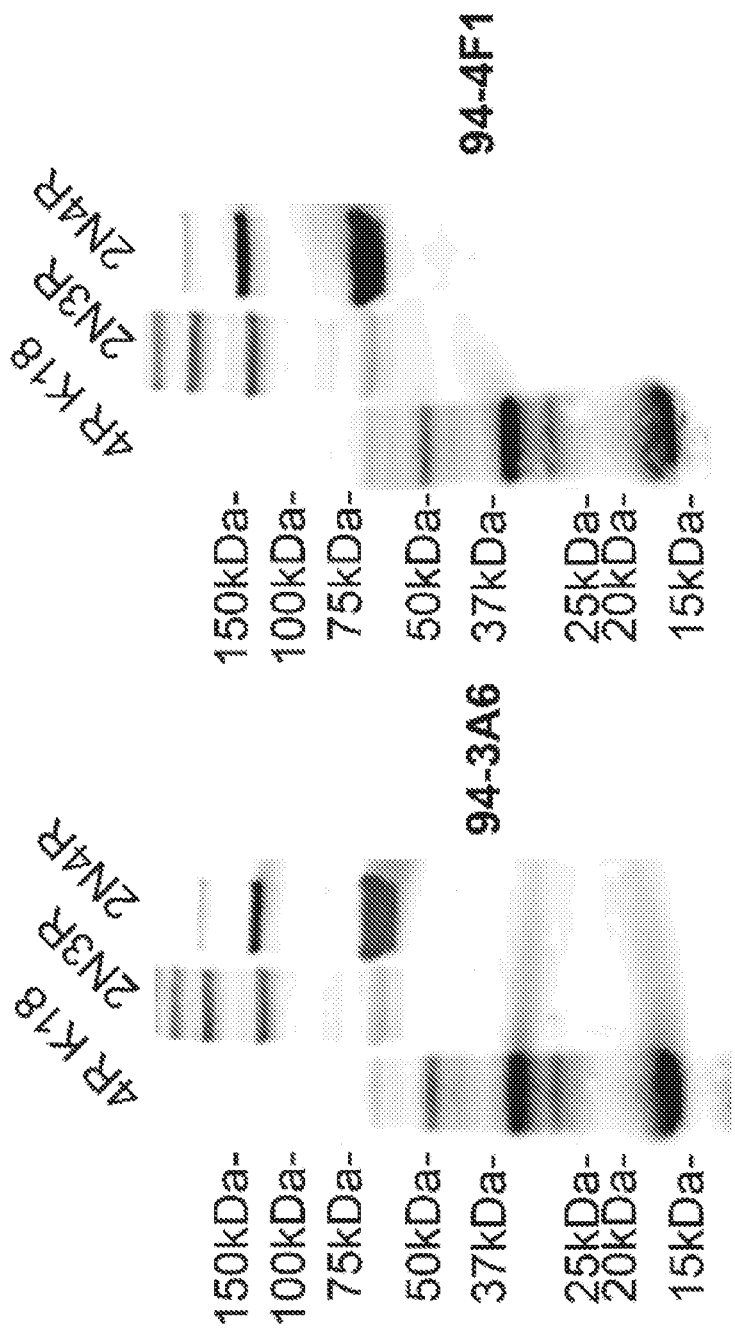

Example 1: Generation of Antibodies Targeting the Microtubule Binding Domain of Tau Mice were immunized with the synthetic peptides corresponding to the MTBD in 4R human tau 244-372 (K18) conjugated to 21-140 αS at the N-terminus or 21-140 αS at the N-terminus and Aβ1-42 at the C-terminus. Several hybridomas that showed reactivity to recombinant human tau but not to recombinant human αS or AR were identified by ELISA screening. This selectivity for tau was also confirmed by detection of tau pathology by immunohistochemistry of human AD post-mortem brain tissue with abundant tau pathology. Five hybridomas (81A11, 83E4, 94-3A2-2, 94-3A6 and 94-4F1) were identified using these criteria. To map the epitopes of these monoclonal antibodies, immunoblots of recombinant GST tagged human MTBD R1-3, R1, R3 and R4 were probed with these antibodies (FIG. 1). 81A11 recognizes R1-R3 but not R1 or R3 alone highlighting its selectivity for R2. Each of the antibodies 83E4, 94-3A2-2, 94-3A6 and 94-4F1 selectively binds R4 only. The specificity of these monoclonal antibodies was further determined by probing immunoblots of recombinant full-length human 2N/3R and 2N/4R tau and K18 (4R) tau fragment (FIG. 2). 81A11 recognizes both 2N/4R tau and K18 but not 2N/3R tau highlighting its specificity for 4R tau due to its selectivity for R2. Each of the antibodies 83E4, 94-3A2-2, 94-3A6 and 94-4F1 recognize both 3R and 4R tau due to their selectivity for R4.

Figures 3A, 3B, 3C:
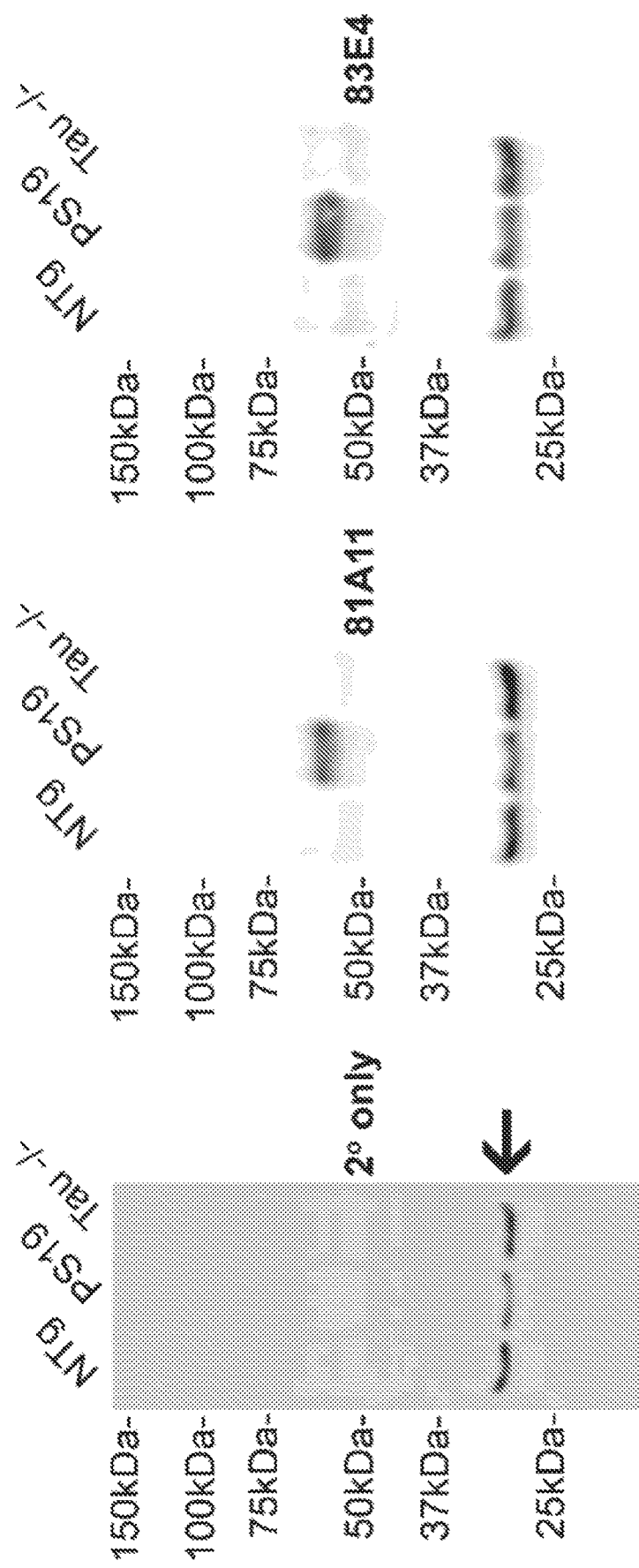
FIGS. 3A to 3F show characterization of the disclosed tau antibodies in NTg, tau KO and PS19 tau Tg mice. Immunoblots of total brain lysates from non-transgenic (NTg), PS19 tau transgenic and tau knock-out (Tau KO) mice were probed with the disclosed tau antibodies 81A11 (FIG. 3B), 83E4 (FIG. 3C), 94-3A2-2 FIG. 3F), 94-3A6 (FIG. 3D), and 94-4F1 (FIG. 3E) to determine affinity for tau in mice. An immunoblot probed with secondary antibody only (FIG. 3A) highlights a non-specific band present on all immunoblots (arrow). The mobilities of molecular mass markers are shown on the left.
Figures 3D, 3E, 3F:
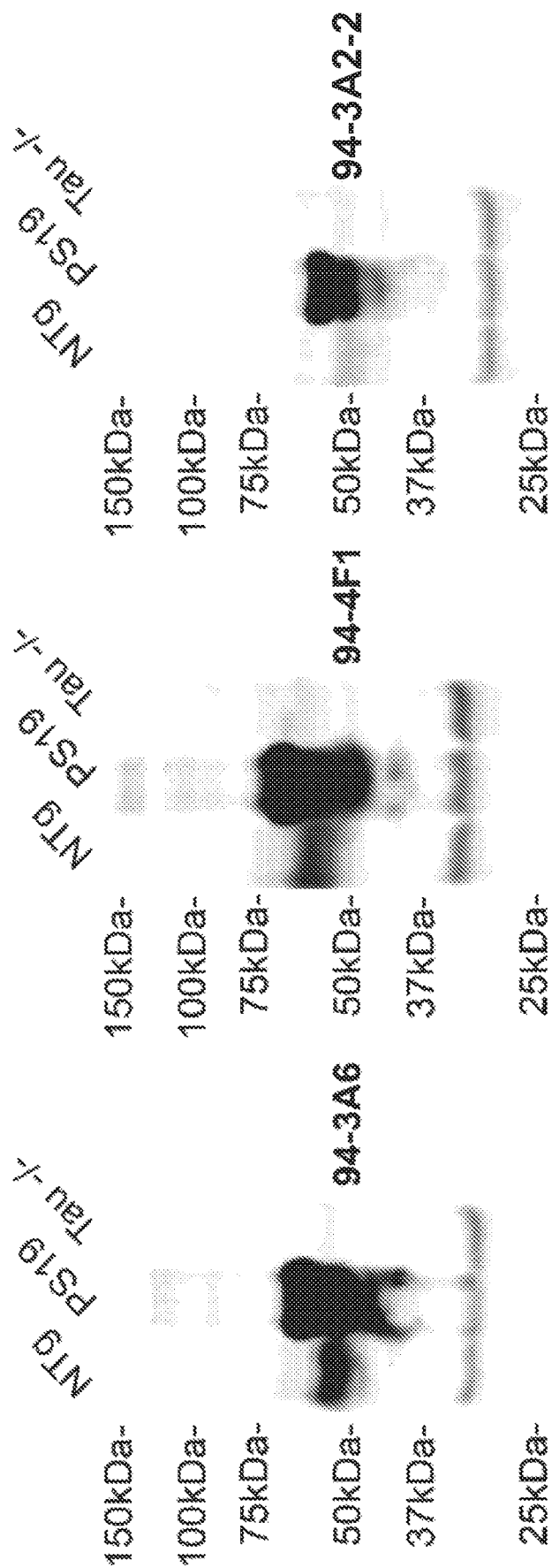
Figure 4A:
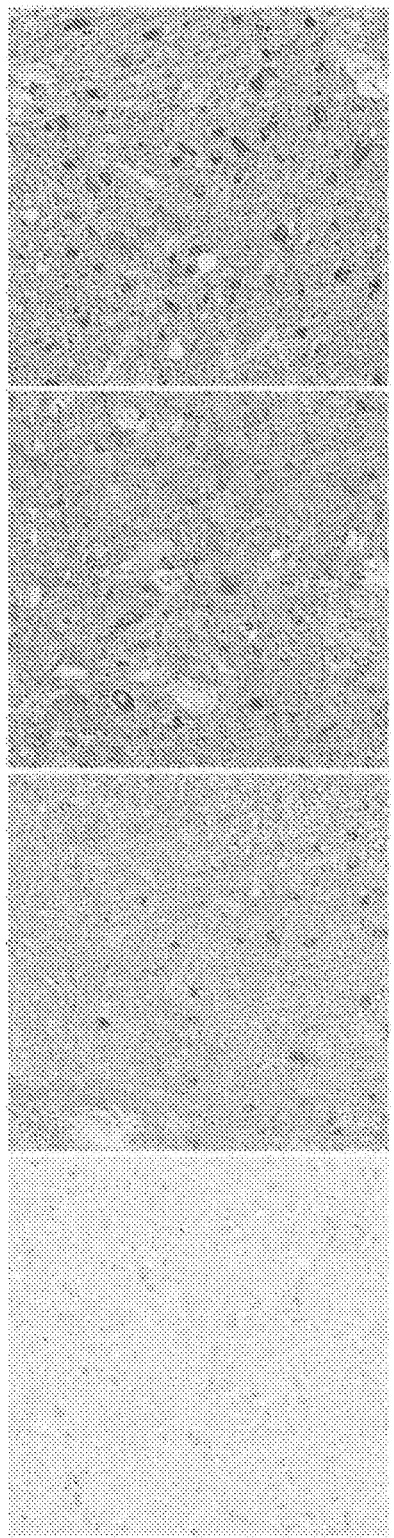
FIGS. 4A to 4E show immunohistological identification of tau inclusions in JNPL3 tau Tg mice and PS19 tau Tg mice. Immunohistochemistry of representative tau pathology in the spinal cord of 7.5 month old JNPL3 Tg mice and 13 month old PS19 Tg mice detected with the disclosed tau antibodies 81A11 (FIG. 4A), 83E4 (FIG. 4B), 94-3A2-2 (FIG. 4C), 94-3A6 (FIG. 4D), and 94-4F1 (FIG. 4E). A seven month old NTg mouse and six month old tau KO mouse are also shown. Scale bar=100 μm.
Figure 4B:
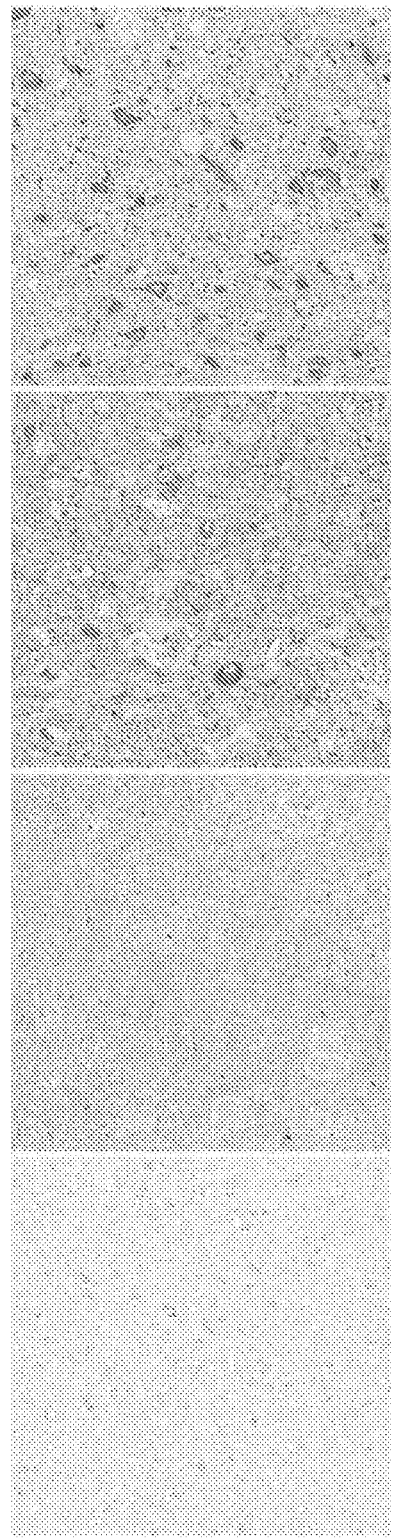
Figure 4C:
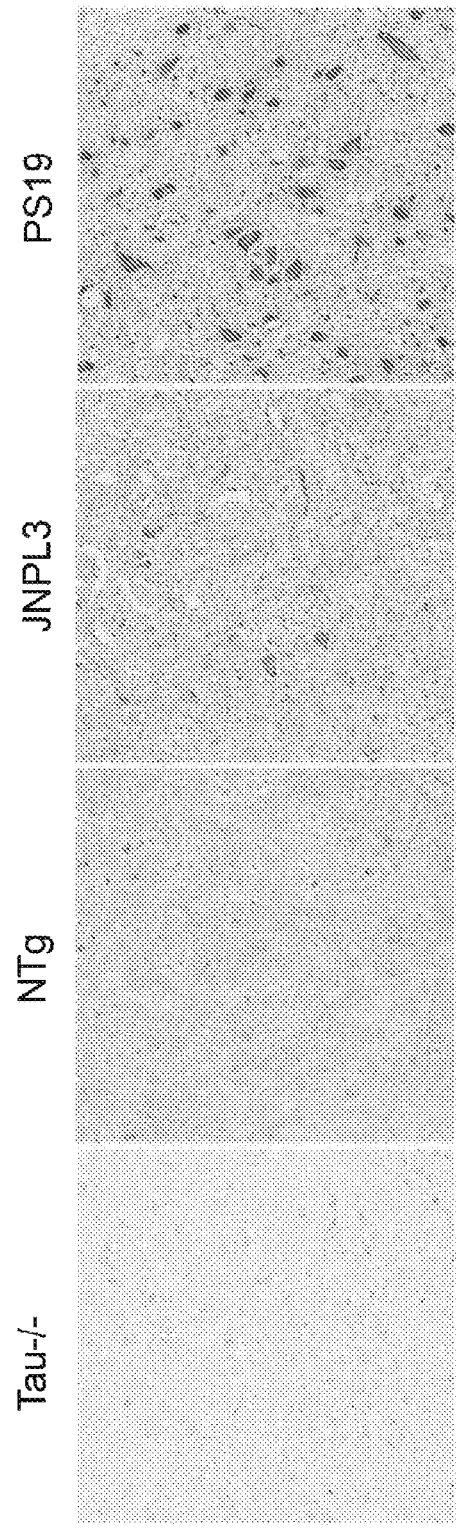
Figure 4D:
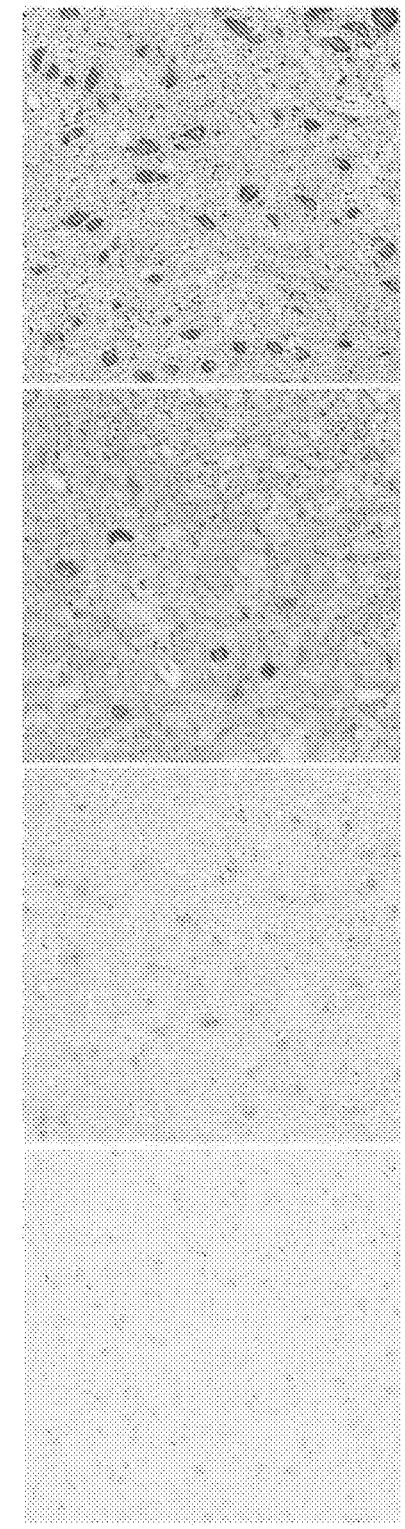
Figure 4E:
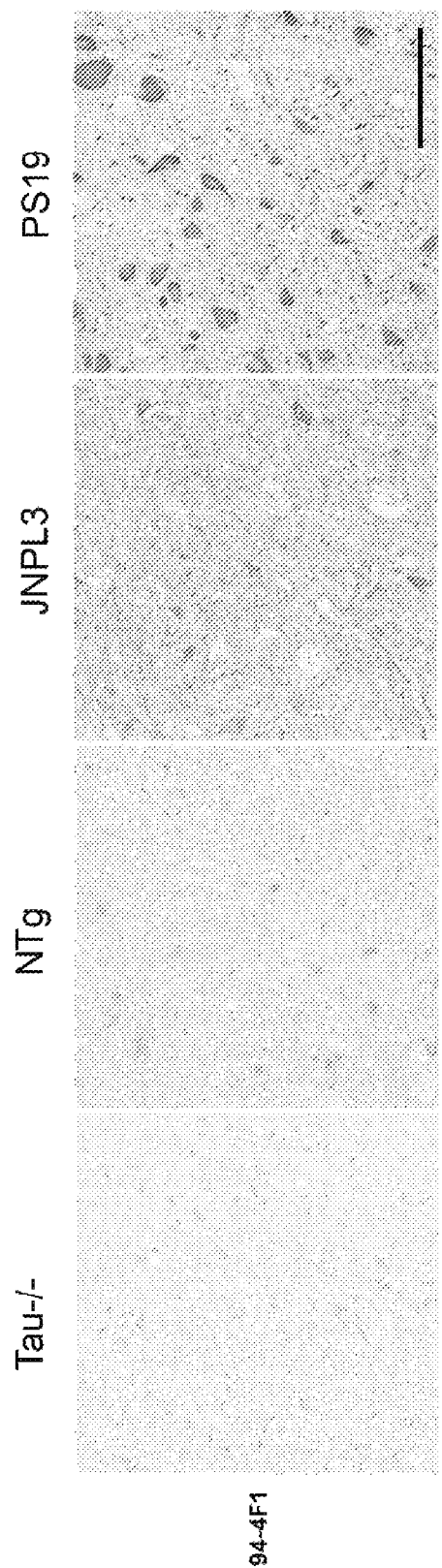

To assess the selectivity of these antibodies for human tau, immunoblots of total mouse brain lysates from tau KO, NTg and PS19 tau Tg mice were probed with these antibodies (FIG. 3). All of these antibodies detected human tau in whole brain lysates from PS19 mice. Antibodies 81A11, 83E4 and 94-3A2-2 reacted weakly with endogenous tau in NTg mice. Antibodies 94-3A6 and 94-4F1 demonstrated stronger reactivity for endogenous tau in NTg mice. All the antibodies were specific for tau as shown using the lysates from tau KO mice. A non-specific band at approximately 30 kDa present in all the lysates was attributed to non-specific binding of the secondary antibody shown with an immunoblot probed only with secondary antibody.

The ability of these new antibodies to react with tau inclusions in the JNPL3 and PS19 mouse model of tauopathy was also examined by immunohistochemistry (FIG. 4). This antibodies described herein detect tau inclusions in the spinal cord of JNPL3 and PS19 mice and detect endogenous tau in an age-matched NTg spinal cord. No reactivity was observed in spinal cord from a tau KO mouse.

Figures 5A, 5B, 5C:
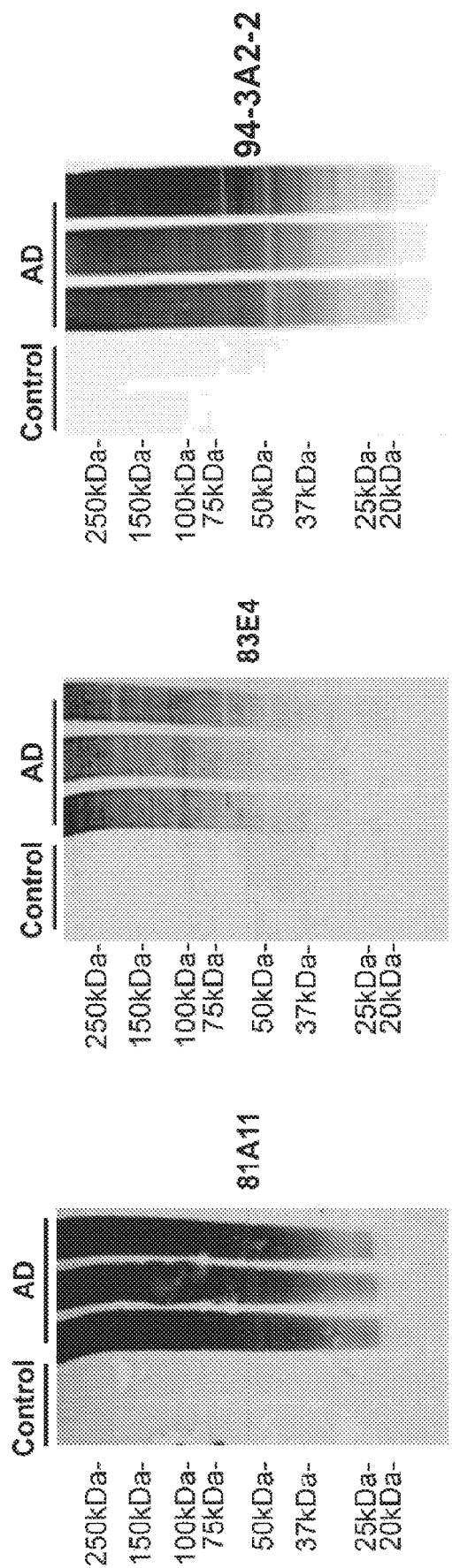
Figure 6A:
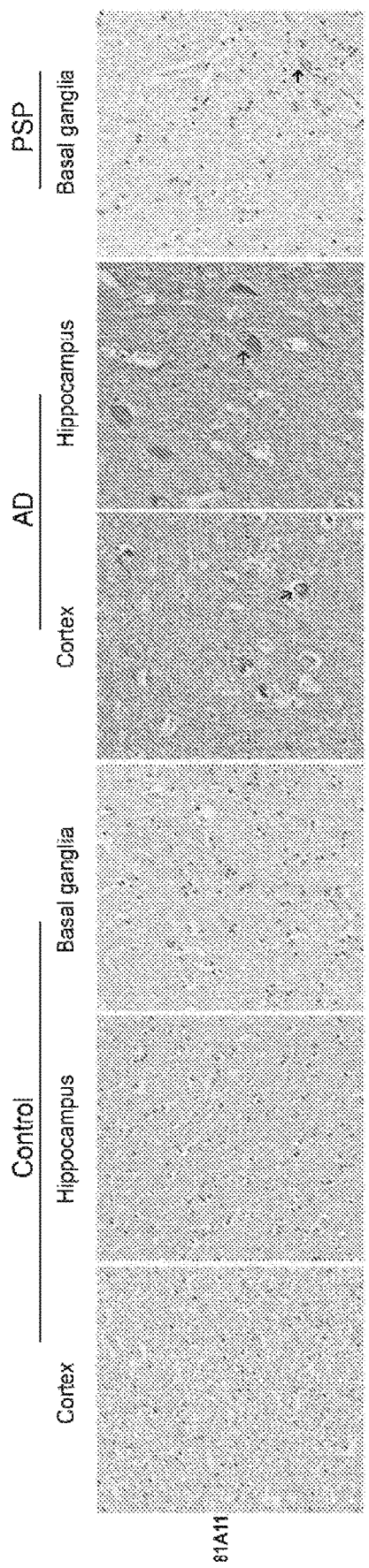
FIGS. 6A to 6E. Immunohistological reactivity of tau inclusions in human post-mortem AD cortex and hippocampus and PSP basal ganglia. Immunohistochemistry of representative tau pathology in post-mortem AD and control temporal cortex and hippocampus and in PSP and control basal ganglia detected with the disclosed tau antibodies 81A11 (FIG. 6A), 83E4 (FIG. 6B), 94-3A2-2 (FIG. 8C), 94-3A6 (FIG. 8D), and 94-4F1 (FIG. 6E). Asterisks mark astroglial tau inclusions and arrows mark NFTs. Scale bar=100 μm.
Figure 6B:
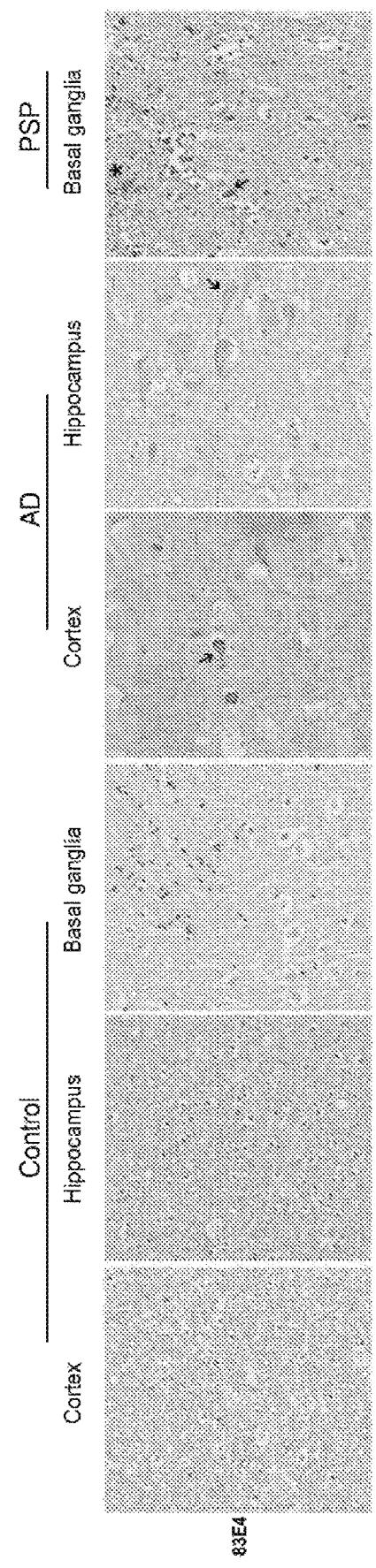
Figure 6C:
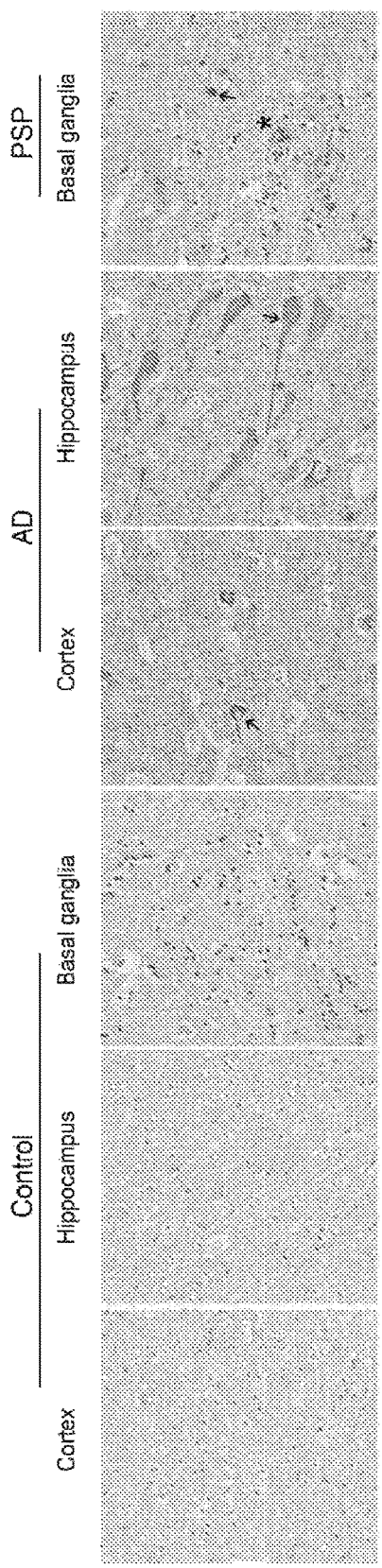
Figure 6D:
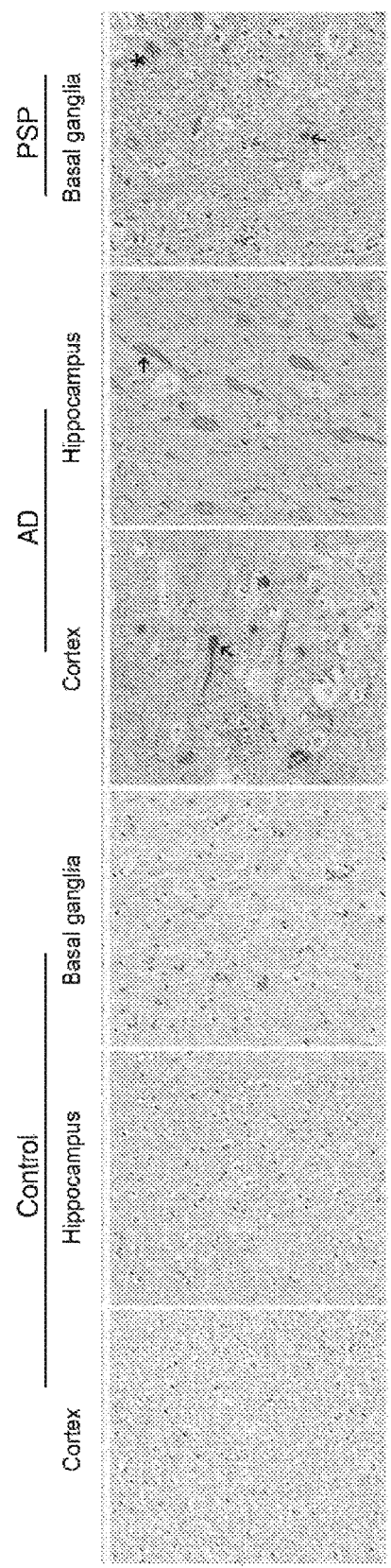
Figure 6E:
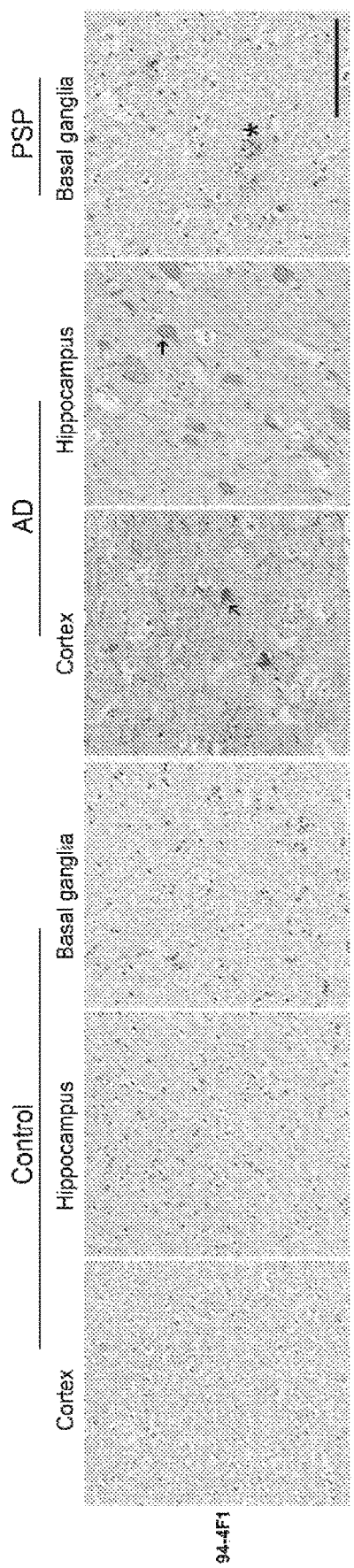

Example 2: Characterization of Antibodies with Human Post-Mortem Ad and Psp Tissue To further characterize the disclosed monoclonal antibodies, sarkosyl-insoluble tau prepared from sequential extractions of temporal cortex tissue from AD and control cases was also assessed by immunoblotting (FIG. 5). All antibodies specifically reacted with sarkosyl-insoluble tau in the AD cases (N=3), showing no reactivity in samples from control cases (N=2). The aggregated and post-translationally modified tau in the AD cases was detected with all these antibodies as proteins smears from below the expected molecular mass of naïve tau to the top of gels.

Neurofibrillary tangles (NFTs) are predominantly found in AD hippocampus and cortex upon histological examination. Therefore, the ability of these antibodies to detect NFTs in AD brain sections was examined by immunohistochemistry (FIG. 6). All of these antibodies reacted with NFTs in AD cortex and hippocampus. In PSP, tau inclusions also form in the glia of the basal ganglia and brain stem, as well as, the development of some globose NFTs. The ability of these antibodies to detect tau inclusions in PSP basal ganglia was examined by immunohistochemistry (FIG. 6). 83E4, 94-3A2-2, 94-3A6 and 94-4F1 highlighted glial tau inclusions and some globose NFTs in PSP sections. 81A11 only weakly detected the tau inclusions in PSP tissue.

Example 3

Monoclonal antibodies that recognize epitopes within the MTBD of tau were generated. These antibodies are highly-specific for tau and show reactivity for pathological inclusions in tauopathy mice and human AD and PSP. A summary of monoclonal tau antibodies disclosed herein is shown in Table 1.

81A11 reacts with R2 and shows selectivity for R4 tau. Each of the 83E4, 94-3A2-2, 94-3A6 and 94-4F1 binds R4 and can recognize 3- and 4-repeat tau. Reactivity of these antibodies with mouse brain tissue was examined by immunohistochemistry and immunoblotting. Each of these monoclonal antibodies shows some reactivity to endogenous mouse tau in the NTg tissue, as 0N4R is the main isoform of tau expressed in adult mice. Each of these antibodies also strongly recognized the over-expressed 1N4R human tau in PS19 brain. These antibodies show no cross-reactivity with tau KO brain demonstrating the high selectivity of these antibodies to tau. In addition, each of these antibodies recognizes NFTs in the spinal cord of JNPL3 and PS19 mice highlighting their utility in recognizing inclusion pathology in these models.

Furthermore, each of these antibodies robustly identifies tau from sarkosyl-insoluble preparations of AD cortical brain tissue by immunoblotting and shows no reactivity with the same lysates prepared from human control cortex. Each of these antibodies also recognizes pathological tau inclusions upon immunohistochemical examination. NFTs and glial and globose NFT inclusions in AD and PSP, respectively, were recognized by each of these antibodies in regions of pathological interest. Endogenous staining of tau was also observed in control cases.

81A11, which recognizes R2 of the MTBD of tau, does not recognize pathological tau inclusions in PSP brain to the same extent as the other antibodies 83E4, 94-3A2-2, 94-3A6 and 94-4F1, each of which recognizes R4. This discrepancy in binding indicates that the epitope for 81A11 is masked due to the amyloidogenic β-sheets forming in this region of tau.

Tau forms its amyloidogenic structure in the MTBD region. Therefore, MTBD region of tau is of therapeutic interest. Indeed, in tau, β-sheet structures flanked by the second (275-280 amino acids of SEQ ID NO: 1) and the third (306-311 amino acids of SEQ ID NO: 1) repeats of MTBD enable the formation of paired and straight helical filaments which are characteristic of tauopathies such as AD and PSP. It is also this region of tau where post-translational modifications permit the disassembly of microtubules, thereby increasing amounts of unbound tau, which can accumulate in the pathological brain.

Effective therapeutic strategies that target tauopathies are not available. There have been numerous failures in anti-Aβ therapies for AD and the correlation between cognitive decline and tau pathology in human AD has driven interest to target tau pathology in AD. Some of these therapies may also be useful for other tauopathies. In particular, the propagation and release of tau is a disease mechanism in AD and other tauopathies. Therefore, immunotherapy intervention with antibodies against tau could prevent the propagation of such pathology. Indeed, several tau immunotherapies have been employed pre-clinically and have shown efficacy in these pre-clinical models. Furthermore, the humanized tau antibody (ABBV-8E12) has received Phase 2 approval for early AD and PSP (Clinical Trial #NCT02880956 and #NCT02985879). Additionally, recent evidence suggests that balancing 3R and 4R tau isoforms is effective in pre-clinical studies and antibodies specific to 3R or 4R tau could enable the rebalancing of tau isoforms.

Tauopathies encompass a diverse spectrum of phenotypes and pathologies. Much interest exists in immunotherapies against tauopathies. The disclosed tau antibodies to the MTBD of tau described herein can be useful in therapeutically targeting tau for treatment of tauopathies.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A recombinant antibody comprising a variable heavy ($V_H$) domain having CDR1, CDR2 and CDR3 sequences and a variable light ($V_L$) domain having CDR1, CDR2 and CDR3 sequences, wherein the CDR1 sequence of the $V_H$ domain comprises the amino acid sequence SEQ ID NO:26; the CDR2 sequence of the $V_H$ domain comprises the amino acid sequence SEQ ID NO:27; the CDR3 sequence of the $V_H$ domain comprises the amino acid sequence SEQ ID NO:28; the CDR1 sequence of the $V_L$ comprises the amino acid sequence SEQ ID NO:23; the CDR2 sequence of the $V_L$ domain comprises the amino acid sequence SEQ ID NO:24; and the CDR3 sequence of the $V_L$ domain comprises the amino acid sequence SEQ ID NO:25.

2. The antibody of claim 1, wherein the VL domain comprises the amino acid sequence of SEQ ID NO:21 and the VH domain comprises the amino acid sequence of SEQ ID NO:22.

3. The antibody of claim 1, wherein the antibody is conjugated to a label.

4. The antibody of claim 3, wherein the label is selected from an enzyme label, a radioisotope label, a fluorescent label, or a bioluminescent label.

5. The antibody of claim 4, wherein the enzyme label is horseradish peroxidase, alkaline phosphatase, β-galactosidase, luciferase, acetylcholine esterase, or glucose oxidase.

6. The antibody of claim 4, wherein the radioisotope label is selected from the group consisting of $^{125}$I, $^{35}$S, $^{14}$C, $^{32}$P and $^{3}$H.

7. The antibody of claim 4, wherein the fluorescent label is selected from the group consisting of umbelliferone, fluorescein, rhodamine, dichlorotriazinylamine fluorescein, dansyl chloride, fluorescein isothiocyante (FITC), phycoerythrin (PE), Cy5-phycoerythrin (Cy5-PE), Cy7-phycoerythrin (Cy7-PE), allophycocyanin (APC), Cy7-allophycocyanin (Cy7-APC), texas red (TR), and cascade blue.

8. The antibody of claim 4, wherein the bioluminescent label is selected from the group consisting of photoprotein aequorin, adenosine triphosphate, nicotinamide adenine dinucleotide, and D-luciferin.

9. A kit for an immunoassay, comprising the antibody of claim 1, and instructional materials for performing the immunoassay.

10. A method of detecting tau protein in a subject, comprising administering to the subject the antibody of claim 3, and detecting and/or quantifying the antibody or antigen binding fragment thereof bound to tau protein in the subject by positron emission tomography (PET), X-ray computed tomography, single-photon emission computed tomography (SPECT), computed tomography (CT) or computed axial tomography (CAT).

* * * * *

SEQUENCE LISTING

<160> NUMBER OF SEQ ID NOS: 45

<210> SEQ ID NO 1
<211> LENGTH: 441
<212> TYPE: PRT
<213> ORGANISM: Homo sapiens

<400> SEQUENCE: 1

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365
```

```
Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
            435                 440

<210> SEQ ID NO 2
<211> LENGTH: 412
<212> TYPE: PRT
<213> ORGANISM: Homo sapiens

<400> SEQUENCE: 2

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Ile Asn Lys Lys Leu Asp Leu Ser
                245                 250                 255

Asn Val Gln Ser Lys Cys Gly Ser Lys Asp Asn Ile Lys His Val Pro
            260                 265                 270

Gly Gly Gly Ser Val Gln Ile Val Tyr Lys Pro Val Asp Leu Ser Lys
        275                 280                 285

Val Thr Ser Lys Cys Gly Ser Leu Gly Asn Ile His His Lys Pro Gly
    290                 295                 300
```

```
Gly Gly Gln Val Glu Val Lys Ser Glu Lys Leu Asp Phe Lys Asp Arg
305                 310                 315                 320

Val Gln Ser Lys Ile Gly Ser Leu Asp Asn Ile Thr His Val Pro Gly
            325                 330                 335

Gly Gly Asn Lys Lys Ile Glu Thr His Lys Leu Thr Phe Arg Glu Asn
            340                 345                 350

Ala Lys Ala Lys Thr Asp His Gly Ala Glu Ile Val Tyr Lys Ser Pro
            355                 360                 365

Val Val Ser Gly Asp Thr Ser Pro Arg His Leu Ser Asn Val Ser Ser
            370                 375                 380

Thr Gly Ser Ile Asp Met Val Asp Ser Pro Gln Leu Ala Thr Leu Ala
385                 390                 395                 400

Asp Glu Val Ser Ala Ser Leu Ala Lys Gln Gly Leu
                405                 410

<210> SEQ ID NO 3
<211> LENGTH: 383
<212> TYPE: PRT
<213> ORGANISM: Homo sapiens

<400> SEQUENCE: 3

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
            35                  40                  45

Gly Ile Gly Asp Thr Pro Ser Leu Glu Asp Glu Ala Ala Gly His Val
        50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
            115                 120                 125

Glu Pro Pro Lys Ser Gly Asp Arg Ser Gly Tyr Ser Ser Pro Gly Ser
        130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
            195                 200                 205

Lys His Gln Pro Gly Gly Gly Lys Val Gln Ile Ile Asn Lys Lys Leu
        210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
                245                 250                 255

Leu Ser Lys Val Thr Ser Lys Cys Gly Ser Leu Gly Asn Ile His His
            260                 265                 270
```

```
Lys Pro Gly Gly Gly Gln Val Glu Val Lys Ser Glu Lys Leu Asp Phe
            275                 280                 285

Lys Asp Arg Val Gln Ser Lys Ile Gly Ser Leu Asp Asn Ile Thr His
        290                 295                 300

Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
                325                 330                 335

Lys Ser Pro Val Val Ser Gly Asp Thr Ser Pro Arg His Leu Ser Asn
            340                 345                 350

Val Ser Ser Thr Gly Ser Ile Asp Met Val Asp Ser Pro Gln Leu Ala
        355                 360                 365

Thr Leu Ala Asp Glu Val Ser Ala Ser Leu Ala Lys Gln Gly Leu
370                 375                 380

<210> SEQ ID NO 4
<211> LENGTH: 410
<212> TYPE: PRT
<213> ORGANISM: Homo sapiens

<400> SEQUENCE: 4

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270
```

```
Gly Lys Val Gln Ile Val Tyr Lys Pro Val Asp Leu Ser Lys Val Thr
            275                 280                 285

Ser Lys Cys Gly Ser Leu Gly Asn Ile His His Lys Pro Gly Gly Gly
290                 295                 300

Gln Val Glu Val Lys Ser Glu Lys Leu Asp Phe Lys Asp Arg Val Gln
305                 310                 315                 320

Ser Lys Ile Gly Ser Leu Asp Asn Ile Thr His Val Pro Gly Gly Gly
            325                 330                 335

Asn Lys Lys Ile Glu Thr His Lys Leu Thr Phe Arg Glu Asn Ala Lys
            340                 345                 350

Ala Lys Thr Asp His Gly Ala Glu Ile Val Tyr Lys Ser Pro Val Val
            355                 360                 365

Ser Gly Asp Thr Ser Pro Arg His Leu Ser Asn Val Ser Ser Thr Gly
370                 375                 380

Ser Ile Asp Met Val Asp Ser Pro Gln Leu Ala Thr Leu Ala Asp Glu
385                 390                 395                 400

Val Ser Ala Ser Leu Ala Lys Gln Gly Leu
            405                 410

<210> SEQ ID NO 5
<211> LENGTH: 381
<212> TYPE: PRT
<213> ORGANISM: Homo sapiens

<400> SEQUENCE: 5

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240
```

```
Pro Gly Gly Gly Lys Val Gln Ile Val Tyr Lys Pro Val Asp Leu Ser
            245                 250                 255

Lys Val Thr Ser Lys Cys Gly Ser Leu Gly Asn Ile His His Lys Pro
        260                 265                 270

Gly Gly Gly Gln Val Glu Val Lys Ser Glu Lys Leu Asp Phe Lys Asp
        275                 280                 285

Arg Val Gln Ser Lys Ile Gly Ser Leu Asp Asn Ile Thr His Val Pro
        290                 295                 300

Gly Gly Gly Asn Lys Lys Ile Glu Thr His Lys Leu Thr Phe Arg Glu
305                 310                 315                 320

Asn Ala Lys Ala Lys Thr Asp His Gly Ala Glu Ile Val Tyr Lys Ser
                325                 330                 335

Pro Val Val Ser Gly Asp Thr Ser Pro Arg His Leu Ser Asn Val Ser
            340                 345                 350

Ser Thr Gly Ser Ile Asp Met Val Asp Ser Pro Gln Leu Ala Thr Leu
            355                 360                 365

Ala Asp Glu Val Ser Ala Ser Leu Ala Lys Gln Gly Leu
        370                 375                 380

<210> SEQ ID NO 6
<211> LENGTH: 352
<212> TYPE: PRT
<213> ORGANISM: Homo sapiens

<400> SEQUENCE: 6

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Val Tyr Lys Pro Val
    210                 215                 220

Asp Leu Ser Lys Val Thr Ser Lys Cys Gly Ser Leu Gly Asn Ile His
225                 230                 235                 240
```

```
His Lys Pro Gly Gly Gly Gln Val Glu Val Lys Ser Glu Lys Leu Asp
                245                 250                 255

Phe Lys Asp Arg Val Gln Ser Lys Ile Gly Ser Leu Asp Asn Ile Thr
            260                 265                 270

His Val Pro Gly Gly Gly Asn Lys Lys Ile Glu Thr His Lys Leu Thr
        275                 280                 285

Phe Arg Glu Asn Ala Lys Ala Lys Thr Asp His Gly Ala Glu Ile Val
    290                 295                 300

Tyr Lys Ser Pro Val Val Ser Gly Asp Thr Ser Pro Arg His Leu Ser
305                 310                 315                 320

Asn Val Ser Ser Thr Gly Ser Ile Asp Met Val Asp Ser Pro Gln Leu
                325                 330                 335

Ala Thr Leu Ala Asp Glu Val Ser Ala Ser Leu Ala Lys Gln Gly Leu
            340                 345                 350

<210> SEQ ID NO 7
<211> LENGTH: 93
<212> TYPE: PRT
<213> ORGANISM: Artificial Sequence
<220> FEATURE:
<223> OTHER INFORMATION: residues 244-336 of 0N4R tau

<400> SEQUENCE: 7

Gln Thr Ala Pro Val Pro Met Pro Asp Leu Lys Asn Val Lys Ser Lys
1               5                   10                  15

Ile Gly Ser Thr Glu Asn Leu Lys His Gln Pro Gly Gly Gly Lys Val
            20                  25                  30

Gln Ile Ile Asn Lys Lys Leu Asp Leu Ser Asn Val Gln Ser Lys Cys
        35                  40                  45

Gly Ser Lys Asp Asn Ile Lys His Val Pro Gly Gly Gly Ser Val Gln
    50                  55                  60

Ile Val Tyr Lys Pro Val Asp Leu Ser Lys Val Thr Ser Lys Cys Gly
65                  70                  75                  80

Ser Leu Gly Asn Ile His His Lys Pro Gly Gly Gly Gln
                85                  90

<210> SEQ ID NO 8
<211> LENGTH: 31
<212> TYPE: PRT
<213> ORGANISM: Artificial Sequence
<220> FEATURE:
<223> OTHER INFORMATION: residues 244 -274 of 0N4R tau

<400> SEQUENCE: 8

Gln Thr Ala Pro Val Pro Met Pro Asp Leu Lys Asn Val Lys Ser Lys
1               5                   10                  15

Ile Gly Ser Thr Glu Asn Leu Lys His Gln Pro Gly Gly Gly Lys
            20                  25                  30

<210> SEQ ID NO 9
<211> LENGTH: 31
<212> TYPE: PRT
<213> ORGANISM: Artificial Sequence
<220> FEATURE:
<223> OTHER INFORMATION: residues 275-305 of 0N/4R tau
```

```
<400> SEQUENCE: 9

Val Gln Ile Ile Asn Lys Lys Leu Asp Leu Ser Asn Val Gln Ser Lys
1               5                   10                  15

Cys Gly Ser Lys Asp Asn Ile Lys His Val Pro Gly Gly Gly Ser
            20                  25                  30

<210> SEQ ID NO 10
<211> LENGTH: 31
<212> TYPE: PRT
<213> ORGANISM: Artificial Sequence
<220> FEATURE:
<223> OTHER INFORMATION: residues 306-336 of 0N/4R tau

<400> SEQUENCE: 10

Val Gln Ile Val Tyr Lys Pro Val Asp Leu Ser Lys Val Thr Ser Lys
1               5                   10                  15

Cys Gly Ser Leu Gly Asn Ile His His Lys Pro Gly Gly Gly Gln
            20                  25                  30

<210> SEQ ID NO 11
<211> LENGTH: 36
<212> TYPE: PRT
<213> ORGANISM: Artificial Sequence
<220> FEATURE:
<223> OTHER INFORMATION: residues 337-372 of 0N/4R tau

<400> SEQUENCE: 11

Val Glu Val Lys Ser Glu Lys Leu Asp Phe Lys Asp Arg Val Gln Ser
1               5                   10                  15

Lys Ile Gly Ser Leu Asp Asn Ile Thr His Val Pro Gly Gly Gly Asn
            20                  25                  30

Lys Lys Ile Glu
        35

<210> SEQ ID NO 12
<211> LENGTH: 129
<212> TYPE: PRT
<213> ORGANISM: Artificial Sequence
<220> FEATURE:
<223> OTHER INFORMATION: residues 244-372 of 0N/4R tau

<400> SEQUENCE: 12

Gln Thr Ala Pro Val Pro Met Pro Asp Leu Lys Asn Val Lys Ser Lys
1               5                   10                  15

Ile Gly Ser Thr Glu Asn Leu Lys His Gln Pro Gly Gly Gly Lys Val
            20                  25                  30

Gln Ile Ile Asn Lys Lys Leu Asp Leu Ser Asn Val Gln Ser Lys Cys
        35                  40                  45

Gly Ser Lys Asp Asn Ile Lys His Val Pro Gly Gly Gly Ser Val Gln
    50                  55                  60

Ile Val Tyr Lys Pro Val Asp Leu Ser Lys Val Thr Ser Lys Cys Gly
65                  70                  75                  80

Ser Leu Gly Asn Ile His His Lys Pro Gly Gly Gly Gln Val Glu Val
                85                  90                  95

Lys Ser Glu Lys Leu Asp Phe Lys Asp Arg Val Gln Ser Lys Ile Gly
            100                 105                 110

Ser Leu Asp Asn Ile Thr His Val Pro Gly Gly Gly Asn Lys Lys Ile
        115                 120                 125

Glu
```

<210> SEQ ID NO 13
<211> LENGTH: 138
<212> TYPE: PRT
<213> ORGANISM: Mus musculus

<400> SEQUENCE: 13

Asp Ile Val Leu Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val
    130                 135

<210> SEQ ID NO 14
<211> LENGTH: 113
<212> TYPE: PRT
<213> ORGANISM: Mus musculus

<400> SEQUENCE: 14

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Ile His Trp Val Lys Gln Thr Pro Val Tyr Gly Leu Glu Trp Ile
        35                  40                  45

Gly Ala Ile Asp Pro Glu Thr Asp Thr Ile Asp Phe Asn Gln Lys Phe
    50                  55                  60

Lys Gly Lys Ala Ile Leu Thr Ala Asp Lys Ser Ser Ser Thr Ala Tyr
65                  70                  75                  80

Met Glu Leu Arg Ser Leu Thr Ser Glu Asp Ser Ala Val Tyr Tyr Ser
                85                  90                  95

Leu His Trp Asp Tyr Trp Gly Gln Gly Thr Thr Leu Thr Val Ser Ser
            100                 105                 110

Ala

<210> SEQ ID NO 15
<211> LENGTH: 10
<212> TYPE: PRT
<213> ORGANISM: Artificial Sequence
<220> FEATURE:
<223> OTHER INFORMATION: CDR1 sequence of light chain of antibody 81A11

<400> SEQUENCE: 15

Lys Ser Val Ser Thr Ser Gly Tyr Ser Tyr
1               5                   10

```
<210> SEQ ID NO 16
<211> LENGTH: 4
<212> TYPE: PRT
<213> ORGANISM: Artificial Sequence
<220> FEATURE:
<223> OTHER INFORMATION: CDR2 sequence of light chain of antibody 81A11

<400> SEQUENCE: 16

Leu Val Ser Asn
1

<210> SEQ ID NO 17
<211> LENGTH: 14
<212> TYPE: PRT
<213> ORGANISM: Artificial Sequence
<220> FEATURE:
<223> OTHER INFORMATION: CDR3 sequence of light chain of antibody 81A11

<400> SEQUENCE: 17

Gln His Ile Arg Glu Leu Thr Arg Ser Glu Gly Gly Pro Ser
1               5                   10

<210> SEQ ID NO 18
<211> LENGTH: 8
<212> TYPE: PRT
<213> ORGANISM: Artificial Sequence
<220> FEATURE:
<223> OTHER INFORMATION: CDR1 sequence of heavy chain of antibody 81A11

<400> SEQUENCE: 18

Gly Tyr Thr Phe Thr Asp Tyr Glu
1               5

<210> SEQ ID NO 19
<211> LENGTH: 8
<212> TYPE: PRT
<213> ORGANISM: Artificial Sequence
<220> FEATURE:
<223> OTHER INFORMATION: CDR2 sequence of heavy chain of antibody 81A11

<400> SEQUENCE: 19

Ile Asp Pro Glu Thr Asp Thr Ile
1               5

<210> SEQ ID NO 20
<211> LENGTH: 5
<212> TYPE: PRT
<213> ORGANISM: Artificial Sequence
<220> FEATURE:
<223> OTHER INFORMATION: CDR3 sequence of heavy chain of antibody 81A11

<400> SEQUENCE: 20

Ser Leu His Trp Asp
1               5

<210> SEQ ID NO 21
<211> LENGTH: 132
<212> TYPE: PRT
<213> ORGANISM: Mus musculus

<400> SEQUENCE: 21

Glu Asn Val Leu Thr Gln Ser Pro Ala Ile Met Ser Ala Ser Pro Gly
1               5                   10                  15

Glu Lys Val Thr Met Thr Cys Ser Ala Ser Ser Asn Val Asn Tyr Met
            20                  25                  30
```

His Trp Phe Gln Gln Glu Ser Thr Ser Pro Lys Leu Trp Ile Tyr
            35                  40                  45

Asp Thr Ser Lys Leu Ala Ser Gly Val Pro Arg Phe Ser Gly Ser
 50                  55                  60

Gly Ser Gly Asn Ser Tyr Ser Leu Thr Ile Ser Ser Met Glu Ala Glu
 65                  70                  75                  80

Asp Val Ala Thr Tyr Tyr Cys Phe Gln Gly Ser Gly Tyr Pro Tyr Thr
                 85                  90                  95

Phe Gly Gly Gly Thr Lys Leu Glu Ile Lys Arg Ala Asp Ala Ala Pro
             100                 105                 110

Thr Val Ser Ile Phe Pro Pro Ser Ser Glu Gln Leu Thr Ser Gly Gly
             115                 120                 125

Ala Ser Val Val
    130

<210> SEQ ID NO 22
<211> LENGTH: 113
<212> TYPE: PRT
<213> ORGANISM: Mus musculus

<400> SEQUENCE: 22

Gln Val Gln Leu Gln Gln Pro Gly Thr Glu Leu Val Lys Pro Gly Ala
 1               5                  10                  15

Ser Val Lys Leu Ser Cys Lys Ala Ser Gly Tyr Pro Phe Thr Asn Tyr
             20                  25                  30

Trp Met His Trp Val Lys Gln Arg Pro Gly Gln Gly Leu Glu Trp Ile
         35                  40                  45

Gly Asn Ile Asn Pro Thr Asn Gly Asp Thr Asn Tyr Asn Glu Lys Phe
     50                  55                  60

Lys Ser Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Thr Arg Val Thr Tyr Trp Gly Gln Gly Thr Thr Leu Thr Val Ser Ser
             100                 105                 110

Ala

<210> SEQ ID NO 23
<211> LENGTH: 5
<212> TYPE: PRT
<213> ORGANISM: Artificial Sequence
<220> FEATURE:
<223> OTHER INFORMATION: CDR1 sequence of light chain of antibody 94-3A6

<400> SEQUENCE: 23

Ser Asn Val Asn Tyr
 1               5

<210> SEQ ID NO 24
<211> LENGTH: 4
<212> TYPE: PRT
<213> ORGANISM: Artificial Sequence
<220> FEATURE:
<223> OTHER INFORMATION: CDR2 sequence of light chain of antibody 94-3A6

<400> SEQUENCE: 24

Asp Thr Ser Lys
 1

```
<210> SEQ ID NO 25
<211> LENGTH: 7
<212> TYPE: PRT
<213> ORGANISM: Artificial Sequence
<220> FEATURE:
<223> OTHER INFORMATION: CDR3 sequence of light chain of antibody 94-3A6

<400> SEQUENCE: 25

Phe Gln Gly Ser Gly Tyr Pro
1               5

<210> SEQ ID NO 26
<211> LENGTH: 8
<212> TYPE: PRT
<213> ORGANISM: Artificial Sequence
<220> FEATURE:
<223> OTHER INFORMATION: CDR1 sequence of heavy chain of antibody 94-3A6

<400> SEQUENCE: 26

Gly Tyr Pro Phe Thr Asn Tyr Trp
1               5

<210> SEQ ID NO 27
<211> LENGTH: 8
<212> TYPE: PRT
<213> ORGANISM: Artificial Sequence
<220> FEATURE:
<223> OTHER INFORMATION: CDR2 sequence of heavy chain of antibody 94-3A6

<400> SEQUENCE: 27

Ile Asn Pro Thr Asn Gly Asp Thr
1               5

<210> SEQ ID NO 28
<211> LENGTH: 5
<212> TYPE: PRT
<213> ORGANISM: Artificial Sequence
<220> FEATURE:
<223> OTHER INFORMATION: CDR3 sequence of heavy chain of antibody 94-3A6

<400> SEQUENCE: 28

Cys Thr Arg Val Thr
1               5

<210> SEQ ID NO 29
<211> LENGTH: 139
<212> TYPE: PRT
<213> ORGANISM: Mus musculus

<400> SEQUENCE: 29

Asp Ile Val Leu Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp Lys Lys Leu Glu Ile
            100                 105                 110
```

```
Lys Arg Ala Asp Ala Ala Pro Thr Val Ser Ile Phe Pro Pro Ser Ser
        115                 120                 125

Glu Gln Leu Thr Ser Gly Gly Ala Ser Val Val
    130                 135

<210> SEQ ID NO 30
<211> LENGTH: 113
<212> TYPE: PRT
<213> ORGANISM: Mus musculus

<400> SEQUENCE: 30

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Thr Tyr
            20                  25                  30

Trp Met His Trp Ile Lys Gln Arg Pro Gly Gln Gly Leu Glu Trp Ile
        35                  40                  45

Gly Tyr Ile Asn Pro Ser Asn Asp Tyr Thr Glu Tyr Asn Gln Lys Phe
    50                  55                  60

Lys Asp Glu Ala Thr Leu Thr Val Asp Lys Ser Ser Ser Thr Ala Tyr
65                  70                  75                  80

Met Gln Leu Asn Ser Leu Ile Ser Glu Asp Ser Ala Val Tyr Tyr Cys
                85                  90                  95

Ala His Pro Ala Tyr Trp Gly Gln Gly Thr Leu Val Thr Val Ser Pro
            100                 105                 110

Ala

<210> SEQ ID NO 31
<211> LENGTH: 10
<212> TYPE: PRT
<213> ORGANISM: Artificial Sequence
<220> FEATURE:
<223> OTHER INFORMATION: CDR1 sequence of light chain of antibody 94-3A2

<400> SEQUENCE: 31

Lys Ser Val Ser Thr Ser Gly Tyr Ser Tyr
1               5                   10

<210> SEQ ID NO 32
<211> LENGTH: 4
<212> TYPE: PRT
<213> ORGANISM: Artificial Sequence
<220> FEATURE:
<223> OTHER INFORMATION: CDR2 sequence of light chain of antibody 94-3A2

<400> SEQUENCE: 32

Leu Val Ser Asn
1

<210> SEQ ID NO 33
<211> LENGTH: 14
<212> TYPE: PRT
<213> ORGANISM: Artificial Sequence
<220> FEATURE:
<223> OTHER INFORMATION: CDR3 sequence of light chain of antibody 94-3A2

<400> SEQUENCE: 33

Gln His Ile Arg Glu Leu Thr Arg Ser Glu Gly Gly Pro Ser
1               5                   10
```

```
<210> SEQ ID NO 34
<211> LENGTH: 8
<212> TYPE: PRT
<213> ORGANISM: Artificial Sequence
<220> FEATURE:
<223> OTHER INFORMATION: CDR1 sequence of heavy chain of antibody 94-3A2

<400> SEQUENCE: 34

Gly Tyr Thr Phe Thr Thr Tyr Trp
1               5

<210> SEQ ID NO 35
<211> LENGTH: 8
<212> TYPE: PRT
<213> ORGANISM: Artificial Sequence
<220> FEATURE:
<223> OTHER INFORMATION: CDR2 sequence of heavy chain of antibody 94-3A2

<400> SEQUENCE: 35

Ile Asn Pro Ser Asn Asp Tyr Thr
1               5

<210> SEQ ID NO 36
<211> LENGTH: 5
<212> TYPE: PRT
<213> ORGANISM: Artificial Sequence
<220> FEATURE:
<223> OTHER INFORMATION: CDR3 sequence of heavy chain of antibody 94-3A2

<400> SEQUENCE: 36

Cys Ala His Pro Ala
1               5

<210> SEQ ID NO 37
<211> LENGTH: 4
<212> TYPE: PRT
<213> ORGANISM: Artificial Sequence
<220> FEATURE:
<223> OTHER INFORMATION: tetrapeptide which prevents the intrabody from
      being secreted from the ER

<400> SEQUENCE: 37

Lys Asp Glu Leu
1

<210> SEQ ID NO 38
<211> LENGTH: 132
<212> TYPE: PRT
<213> ORGANISM: Mus musculus

<400> SEQUENCE: 38

Glu Asn Val Leu Thr Gln Ser Pro Ala Ile Met Ser Ala Ser Pro Gly
1               5                   10                  15

Glu Lys Val Thr Met Thr Cys Ser Ala Ser Ser Val Asn Tyr Met
            20                  25                  30

His Trp Tyr Gln Gln Lys Ser Gly Thr Ser Pro Lys Leu Trp Ile Tyr
        35                  40                  45

Asp Thr Ser Lys Leu Ala Ser Gly Val Pro Gly Arg Phe Ser Gly Ser
    50                  55                  60

Gly Ser Gly Asn Ser Tyr Ser Leu Thr Ile Ser Ser Met Glu Ala Glu
65                  70                  75                  80

Asp Val Ala Thr Tyr Tyr Cys Phe Gln Gly Ser Gly Tyr Pro Phe Thr
                85                  90                  95
```

```
Phe Gly Ser Gly Thr Lys Leu Glu Ile Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val
    130

<210> SEQ ID NO 39
<211> LENGTH: 113
<212> TYPE: PRT
<213> ORGANISM: Mus musculus

<400> SEQUENCE: 39

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Thr Tyr
            20                  25                  30

Trp Met His Trp Ile Lys Gln Arg Pro Gly Gln Gly Leu Glu Trp Ile
        35                  40                  45

Gly Tyr Ile Asn Pro Ser Asn Asp Tyr Thr Glu Tyr Asn Gln Lys Phe
    50                  55                  60

Lys Asp Glu Ala Thr Leu Thr Val Asp Lys Ser Ser Ser Thr Ala Tyr
65                  70                  75                  80

Met Gln Leu Asn Ser Leu Ile Ser Glu Asp Ser Ala Val Tyr Tyr Cys
                85                  90                  95

Ala His Pro Ala Tyr Trp Gly Gln Gly Thr Leu Val Thr Val Ser Ser
            100                 105                 110

Ala

<210> SEQ ID NO 40
<211> LENGTH: 5
<212> TYPE: PRT
<213> ORGANISM: Artificial Sequence
<220> FEATURE:
<223> OTHER INFORMATION: CDR1 sequence of light chain of antibody
      94-3A2-2

<400> SEQUENCE: 40

Ser Ser Val Asn Tyr
1               5

<210> SEQ ID NO 41
<211> LENGTH: 4
<212> TYPE: PRT
<213> ORGANISM: Artificial Sequence
<220> FEATURE:
<223> OTHER INFORMATION: CDR2 sequence of light chain of antibody
      94-3A2-2

<400> SEQUENCE: 41

Asp Thr Ser Lys
1

<210> SEQ ID NO 42
<211> LENGTH: 7
<212> TYPE: PRT
<213> ORGANISM: Artificial Sequence
<220> FEATURE:
<223> OTHER INFORMATION: CDR3 sequence of light chain of antibody
      94-3A2-2
```

```
<400> SEQUENCE: 42

Phe Gln Gly Ser Gly Tyr Pro
1               5

<210> SEQ ID NO 43
<211> LENGTH: 8
<212> TYPE: PRT
<213> ORGANISM: Artificial Sequence
<220> FEATURE:
<223> OTHER INFORMATION: CDR1 sequence of heavy chain of antibody
      94-3A2-2

<400> SEQUENCE: 43

Gly Tyr Thr Phe Thr Thr Tyr Trp
1               5

<210> SEQ ID NO 44
<211> LENGTH: 8
<212> TYPE: PRT
<213> ORGANISM: Artificial Sequence
<220> FEATURE:
<223> OTHER INFORMATION: CDR2 sequence of heavy chain of antibody
      94-3A2-2

<400> SEQUENCE: 44

Ile Asn Pro Ser Asn Asp Tyr Thr
1               5

<210> SEQ ID NO 45
<211> LENGTH: 5
<212> TYPE: PRT
<213> ORGANISM: Artificial Sequence
<220> FEATURE:
<223> OTHER INFORMATION: CDR3 sequence of heavy chain of antibody
      94-3A2-2

<400> SEQUENCE: 45

Cys Ala His Pro Ala
1               5
```